United States Patent
Sapra et al.

(10) Patent No.: US 9,322,042 B2
(45) Date of Patent: Apr. 26, 2016

(54) THERMOSTABLE CELLULASES, AND MUTANTS THEREOF, CAPABLE OF HYDROLYZING CELLULOSE IN IONIC LIQUID

(75) Inventors: Rajat Sapra, Pennington, NJ (US); Supratim Datta, Berkeley, CA (US); Zhiwei Chen, El Cerrito, CA (US); Bradley M. Holmes, Oakland, CA (US); Blake A. Simmons, San Francisco, CA (US); Harvey W. Blanch, San Francisco, CA (US)

(73) Assignees: The Regents of the University of California, Oakland, CA (US); Sandia Corporation, Livermore, CA (US)

( * ) Notice: Subject to any disclaimer, the term of this patent is extended or adjusted under 35 U.S.C. 154(b) by 754 days.

(21) Appl. No.: 13/265,786

(22) PCT Filed: Apr. 23, 2010

(86) PCT No.: PCT/US2010/032320
§ 371 (c)(1),
(2), (4) Date: Jan. 9, 2012

(87) PCT Pub. No.: WO2010/124266
PCT Pub. Date: Oct. 28, 2010

(65) Prior Publication Data
US 2012/0129227 A1   May 24, 2012

Related U.S. Application Data

(60) Provisional application No. 61/172,653, filed on Apr. 24, 2009, provisional application No. 61/172,668, filed on Apr. 24, 2009.

(51) Int. Cl.
*C12P 19/14* (2006.01)
*C12N 15/56* (2006.01)
*C12N 9/42* (2006.01)

(52) U.S. Cl.
CPC .............. *C12P 19/14* (2013.01); *C12N 9/2437* (2013.01); *C12Y 302/01004* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 5,962,258 A † | 10/1999 | Mathur | |
| 6,008,032 A | 12/1999 | Mathur et al. | |
| 6,177,575 B1 | 1/2001 | Arduengo et al. | |
| 6,245,547 B1 | 6/2001 | Mathur et al. | |
| 7,422,876 B2 † | 9/2008 | Short | |
| 7,510,857 B2 * | 3/2009 | Brumm | ............ 435/99 |
| 2008/0227162 A1 | 9/2008 | Varanasi et al. | |

FOREIGN PATENT DOCUMENTS

WO   WO 2007/094852 A2   8/2007

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Accession Q9X273. Nov. 1, 1999.*
Kamiya et al. Epub Feb. 5, 2008. Biotechnol Lett. Jun. 2008;30(6):1037-40.*
Rayne, S. and G. Mazza, "*Trichoderma reesei* derived cellulase activity in three N,N-dimethylethanolammonium akylcarboxylate ionic liquids." Available from *Nature Precedings* <http://hdl.handle.net/10101/npre.2007.632.1> (2007) (posted Aug. 2007).
International Search Report from PCT/US2010/032320, dated Dec. 29, 2010.
Pottkamper et al.; "Applying metagenomics for the identification of bacterial cellulases that are stable in ionic liquids"; *Green Chemistry*; 11(7):957-956 (2009) ePub Apr. 15, 2009.
Rayne and Mazza, Trichoderma reesei derived cellulase activity in three N,N-dimethylethanolammonium alkylcarboxylate ionic liquids, 1-17, Aug. 6, 2007.†

* cited by examiner
† cited by third party

*Primary Examiner* — Christian Fronda
(74) *Attorney, Agent, or Firm* — Kilpatrick Townsend & Stockton LLP

(57) ABSTRACT

The present invention provides for a composition comprising an ionic liquid and a thermostable cellulose, and a method of hydrolyzing a cellulose, comprising: (a) providing a composition comprising a solution comprising an ionic liquid and a cellulose, and (b) introducing a thermostable cellulase to the solution, such that the cellulose is hydrolyzed by the cellulase. The present invention also provides for a *Thermatoga maritima* thermostable cellulase mutant with increased cellulase activity.

15 Claims, 3 Drawing Sheets

SEQUENCE LISTING

```
<160> NUMBER OF SEQ ID NOS: 22

<210> SEQ ID NO 1
<211> LENGTH: 317
<212> TYPE: PRT
<213> ORGANISM: Thermotoga maritima

<400> SEQUENCE: 1

Met Gly Val Asp Pro Phe Glu Arg Asn Lys Ile Leu Gly Arg Gly Ile
1               5                   10                  15

Asn Ile Gly Asn Ala Leu Glu Ala Pro Asn Glu Gly Asp Trp Gly Val
            20                  25                  30

Val Ile Lys Asp Glu Phe Phe Asp Ile Ile Lys Glu Ala Gly Phe Ser
        35                  40                  45

His Val Arg Ile Pro Ile Arg Trp Ser Thr His Ala Tyr Ala Phe Pro
```

```
            50                  55                  60
Pro Tyr Lys Ile Met Asp Arg Phe Phe Lys Arg Val Asp Glu Val Ile
65                  70                  75                  80

Asn Gly Ala Leu Lys Arg Gly Leu Ala Val Val Ile Asn Ile His His
                85                  90                  95

Tyr Ala Glu Leu Met Asn Asp Pro Glu Asp His Lys Glu Arg Phe Leu
            100                 105                 110

Ala Leu Trp Lys Gln Ile Ala Asp Arg Tyr Lys Asp Tyr Pro Glu Thr
        115                 120                 125

Leu Phe Phe Glu Ile Leu Asn Glu Pro His Gly Asn Leu Thr Pro Glu
    130                 135                 140

Lys Trp Asn Glu Leu Leu Glu Glu Ala Leu Lys Val Ile Arg Ser Ile
145                 150                 155                 160

Asp Lys Lys His Thr Ile Ile Ile Gly Thr Ala Glu Trp Gly Gly Ile
                165                 170                 175

Ser Ala Leu Glu Lys Leu Ser Val Pro Lys Trp Glu Lys Asn Ser Ile
            180                 185                 190

Val Thr Ile His Tyr Tyr Asn Pro Phe Glu Phe Thr His Gln Gly Ala
        195                 200                 205

Glu Trp Val Glu Gly Ser Glu Lys Trp Leu Gly Arg Lys Trp Gly Ser
    210                 215                 220

Pro Asp Asp Gln Lys His Leu Ile Glu Glu Phe Asn Phe Ile Glu Glu
225                 230                 235                 240

Trp Ser Lys Lys Asn Lys Arg Pro Ile Tyr Ile Gly Glu Phe Gly Ala
                245                 250                 255

Tyr Arg Lys Ala Asp Leu Glu Ser Arg Ile Lys Trp Thr Ser Phe Val
            260                 265                 270

Val Arg Glu Met Glu Lys Arg Arg Trp Ser Trp Ala Tyr Trp Glu Phe
        275                 280                 285

Cys Ser Gly Phe Gly Val Tyr Asp Thr Leu Arg Lys Thr Trp Asn Lys
    290                 295                 300

Asp Leu Leu Glu Ala Leu Ile Gly Gly Asp Ser Ile Glu
305                 310                 315

<210> SEQ ID NO 2
<211> LENGTH: 317
<212> TYPE: PRT
<213> ORGANISM: Thermotoga maritima

<400> SEQUENCE: 2

Met Gly Val Asp Pro Phe Glu Arg Asn Lys Ile Leu Gly Arg Gly Ile
1               5                   10                  15

Asn Ile Gly Asn Ala Leu Glu Ala Pro Asn Glu Gly Asp Trp Gly Val
            20                  25                  30

Val Ile Lys Asp Glu Phe Phe Asn Ile Ile Lys Glu Ala Gly Phe Ser
        35                  40                  45

His Val Arg Ile Pro Ile Arg Trp Ser Thr His Ala Tyr Ala Phe Pro
    50                  55                  60

Pro Tyr Lys Ile Met Asp Arg Phe Phe Lys Arg Val Asp Glu Val Ile
65                  70                  75                  80

Asn Gly Ala Leu Lys Arg Gly Leu Ala Val Val Ile Asn Ile His His
                85                  90                  95

Tyr Glu Glu Leu Met Asn Asp Pro Glu Glu His Lys Glu Arg Phe Leu
            100                 105                 110
```

```
Ala Leu Trp Lys Gln Ile Ala Asp Arg Tyr Lys Asp Tyr Pro Glu Thr
            115                 120                 125

Leu Phe Phe Glu Ile Leu Asn Glu Pro His Gly Asn Leu Thr Pro Glu
        130                 135                 140

Lys Trp Asn Glu Leu Leu Glu Glu Ala Leu Lys Val Ile Arg Ser Ile
145                 150                 155                 160

Asp Lys Lys His Thr Ile Ile Gly Thr Ala Glu Trp Gly Gly Ile
                165                 170                 175

Ser Ala Leu Glu Lys Leu Ser Val Pro Lys Trp Glu Lys Asn Ser Ile
            180                 185                 190

Val Thr Ile His Tyr Tyr Asn Pro Phe Glu Phe Thr His Gln Gly Ala
        195                 200                 205

Glu Trp Val Glu Gly Ser Glu Lys Trp Leu Gly Arg Lys Trp Gly Ser
    210                 215                 220

Pro Asp Asp Gln Lys His Arg Ile Glu Glu Phe Asn Phe Ile Glu Glu
225                 230                 235                 240

Trp Ser Lys Lys Asn Lys Arg Pro Ile Tyr Ile Gly Glu Phe Gly Ala
                245                 250                 255

Tyr Arg Lys Ala Asp Leu Glu Ser Arg Ile Lys Trp Thr Ser Phe Val
            260                 265                 270

Val Arg Glu Met Glu Lys Arg Arg Trp Ser Trp Ala Tyr Trp Glu Phe
        275                 280                 285

Cys Ser Gly Phe Gly Val Tyr Asp Thr Leu Arg Lys Thr Trp Asn Lys
    290                 295                 300

Asp Leu Leu Glu Ala Leu Ile Gly Gly Asp Ser Ile Glu
305                 310                 315

<210> SEQ ID NO 3
<211> LENGTH: 317
<212> TYPE: PRT
<213> ORGANISM: Thermotoga maritima

<400> SEQUENCE: 3

Met Gly Val Asp Pro Phe Glu Arg Asn Lys Ile Leu Gly Arg Gly Ile
1               5                   10                  15

Asn Ile Gly Asn Ala Leu Glu Ala Pro Asn Glu Gly Asp Trp Gly Val
            20                  25                  30

Val Ile Lys Asp Glu Phe Phe Asp Ile Ile Lys Glu Ala Gly Phe Ser
        35                  40                  45

His Val Arg Ile Pro Ile Arg Trp Ser Thr His Ala Tyr Ala Phe Pro
    50                  55                  60

Pro Tyr Lys Ile Met Asp Arg Phe Phe Lys Arg Val Asp Glu Val Ile
65                  70                  75                  80

Asn Gly Ala Leu Lys Arg Gly Leu Ala Val Val Ile Asn Ile His His
                85                  90                  95

Tyr Glu Glu Leu Met Asn Asp Pro Glu Glu His Lys Glu Arg Phe Leu
            100                 105                 110

Ala Leu Trp Lys Gln Ile Ala Asp Arg Tyr Lys Asp Tyr Pro Glu Thr
        115                 120                 125

Leu Phe Phe Glu Ile Leu Asn Glu Pro His Gly Asn Leu Thr Pro Glu
    130                 135                 140

Lys Trp Asn Glu Leu Leu Glu Glu Ala Leu Lys Val Ile Arg Ser Ile
145                 150                 155                 160

Asp Lys Lys His Thr Ile Ile Gly Thr Ala Glu Trp Gly Gly Ile
                165                 170                 175
```

```
Ser Ala Leu Glu Lys Leu Ser Val Pro Lys Trp Glu Lys Asn Ser Ile
            180                 185                 190

Val Thr Ile His Tyr Tyr Asn Pro Phe Glu Phe Thr His Gln Gly Ala
            195                 200                 205

Glu Trp Val Glu Gly Ser Glu Lys Trp Leu Gly Arg Lys Trp Gly Ser
            210                 215                 220

Pro Asp Asp Gln Lys His Leu Ile Glu Glu Phe Asn Phe Ile Glu Glu
225                 230                 235                 240

Trp Ser Lys Lys Asn Lys Arg Pro Ile Tyr Ile Gly Glu Phe Gly Ala
                245                 250                 255

Tyr Arg Lys Ala Asp Leu Glu Ser Arg Ile Lys Trp Thr Ser Phe Val
            260                 265                 270

Val Arg Glu Met Glu Lys Arg Arg Trp Ser Trp Ala Tyr Trp Glu Phe
            275                 280                 285

Cys Ser Gly Phe Gly Val Tyr Asp Thr Leu Arg Lys Thr Trp Asn Lys
            290                 295                 300

Asp Leu Leu Lys Ala Leu Ile Gly Gly Asp Ser Ile Glu
305                 310                 315

<210> SEQ ID NO 4
<211> LENGTH: 317
<212> TYPE: PRT
<213> ORGANISM: Thermotoga maritima

<400> SEQUENCE: 4

Met Gly Val Asp Pro Phe Glu Arg Asn Lys Ile Leu Gly Arg Gly Ile
1               5                   10                  15

Asn Ile Gly Asn Ala Leu Glu Ala Pro Asn Glu Gly Asp Trp Gly Val
            20                  25                  30

Val Ile Lys Asp Glu Phe Phe Asp Ile Ile Lys Glu Ala Gly Phe Ser
            35                  40                  45

His Val Arg Ile Pro Ile Arg Trp Ser Thr His Ala Tyr Ala Phe Pro
        50                  55                  60

Pro Tyr Lys Ile Met Asp Arg Phe Phe Lys Arg Val Asp Glu Val Ile
65                  70                  75                  80

Asn Gly Ala Leu Lys Arg Gly Leu Ala Val Val Ile Asn Ile His His
                85                  90                  95

Tyr Glu Glu Leu Met Asn Asp Pro Glu His Lys Glu Arg Phe Leu
            100                 105                 110

Ala Leu Trp Lys Gln Ile Ala Asp Arg Tyr Lys Asp Tyr Pro Glu Thr
            115                 120                 125

Leu Phe Phe Glu Ile Leu Asn Glu Pro His Gly Asn Leu Thr Pro Glu
        130                 135                 140

Lys Trp Asn Glu Leu Leu Glu Glu Ala Leu Asn Val Ile Arg Ser Ile
145                 150                 155                 160

Asp Lys Lys His Thr Ile Ile Gly Thr Ala Glu Trp Gly Gly Ile
            165                 170                 175

Ser Ala Leu Glu Lys Leu Ser Val Pro Lys Trp Glu Lys Asn Ser Ile
            180                 185                 190

Val Thr Ile His Tyr Tyr Asn Pro Phe Glu Phe Thr His Gln Gly Ala
            195                 200                 205

Glu Trp Val Glu Gly Ser Glu Lys Trp Leu Gly Arg Lys Trp Gly Ser
            210                 215                 220

Pro Asp Asp Gln Lys His Leu Ile Glu Glu Phe Asn Phe Ile Glu Glu
```

```
                225                 230                 235                 240
Trp Ser Lys Lys Asn Lys Arg Pro Ile Tyr Ile Gly Glu Phe Gly Ala
                    245                 250                 255

Tyr Arg Lys Ala Asp Leu Glu Ser Arg Ile Lys Trp Thr Ser Phe Val
                260                 265                 270

Val Arg Glu Met Glu Lys Arg Arg Trp Ser Trp Ala Tyr Trp Glu Phe
                275                 280                 285

Cys Ser Gly Phe Gly Val Tyr Asp Thr Leu Arg Lys Thr Trp Asn Lys
290                 295                 300

Asp Leu Leu Glu Ala Leu Ile Gly Gly Asp Ser Ile Glu
305                 310                 315

<210> SEQ ID NO 5
<211> LENGTH: 317
<212> TYPE: PRT
<213> ORGANISM: Thermotoga maritima

<400> SEQUENCE: 5

Met Gly Val Asp Pro Phe Glu Arg Asn Lys Ile Leu Gly Arg Gly Ile
1               5                   10                  15

Asn Ile Gly Asn Ala Leu Glu Ala Pro Asn Glu Gly Asp Trp Gly Val
                20                  25                  30

Val Ile Lys Asp Glu Phe Phe Asp Ile Ile Lys Glu Ala Gly Phe Ser
            35                  40                  45

His Val Arg Ile Pro Ile Arg Trp Ser Thr His Ala Tyr Ala Phe Pro
        50                  55                  60

Pro Tyr Lys Ile Met Asp Arg Phe Phe Lys Arg Val Asp Glu Val Ile
65                  70                  75                  80

Asn Gly Ala Leu Lys Arg Gly Leu Ala Val Val Ile Asn Ile His His
                85                  90                  95

Tyr Glu Glu Leu Met Asn Asp Pro Glu His Lys Glu Arg Phe Leu
                100                 105                 110

Val Leu Trp Lys Gln Ile Ala Asp Arg Tyr Lys Asp Tyr Pro Glu Thr
            115                 120                 125

Leu Phe Phe Glu Ile Leu Asn Glu Pro His Gly Asn Leu Thr Pro Glu
        130                 135                 140

Lys Trp Asn Glu Leu Leu Glu Glu Ala Leu Lys Val Ile Arg Ser Ile
145                 150                 155                 160

Asp Lys Lys His Thr Ile Ile Gly Thr Ala Glu Trp Gly Gly Ile
                165                 170                 175

Ser Ala Leu Glu Lys Leu Ser Val Pro Lys Trp Glu Lys Asn Ser Ile
            180                 185                 190

Val Thr Ile His Tyr Tyr Asn Pro Phe Glu Phe Thr His Gln Gly Ala
        195                 200                 205

Glu Trp Val Glu Gly Ser Glu Lys Trp Leu Gly Arg Lys Trp Gly Ser
    210                 215                 220

Pro Asp Asp Gln Lys His Leu Ile Glu Glu Phe Asn Phe Ile Glu Glu
225                 230                 235                 240

Trp Ser Lys Lys Asn Lys Arg Pro Ile Tyr Ile Gly Glu Phe Gly Ala
                245                 250                 255

Tyr Arg Lys Ala Asp Leu Glu Ser Arg Ile Lys Trp Thr Ser Phe Val
                260                 265                 270

Val Arg Glu Met Glu Lys Arg Arg Trp Ser Trp Ala Tyr Trp Glu Phe
            275                 280                 285
```

```
Cys Ser Gly Phe Gly Val Tyr Asp Thr Leu Arg Lys Thr Trp Asn Lys
    290                 295                 300

Asp Leu Leu Glu Ala Leu Ile Gly Gly Asp Ser Ile Glu
305                 310                 315

<210> SEQ ID NO 6
<211> LENGTH: 317
<212> TYPE: PRT
<213> ORGANISM: Thermotoga maritima

<400> SEQUENCE: 6

Met Gly Val Asp Pro Phe Glu Arg Asn Lys Ile Leu Gly Arg Gly Ile
1               5                   10                  15

Asn Ile Gly Asn Ala Leu Glu Ala Pro Asn Glu Gly Asp Trp Gly Val
                20                  25                  30

Val Ile Lys Asp Glu Phe Phe Asp Ile Ile Lys Glu Ala Gly Phe Ser
            35                  40                  45

His Val Arg Ile Pro Ile Arg Trp Ser Thr His Ala Tyr Ala Phe Pro
        50                  55                  60

Pro Tyr Lys Ile Met Asp Arg Phe Lys Arg Val Asp Glu Val Ile
65                  70                  75                  80

Asn Gly Ala Leu Lys Arg Gly Leu Ala Val Val Ile Asn Ile His His
                85                  90                  95

Tyr Glu Glu Leu Met Asn Asp Pro Glu Glu His Lys Gly Arg Phe Leu
            100                 105                 110

Ala Leu Trp Lys Gln Ile Ala Asp Arg Tyr Lys Asp Tyr Pro Glu Thr
        115                 120                 125

Leu Phe Phe Asp Ile Leu Asn Glu Pro His Gly Ser Leu Thr Pro Glu
    130                 135                 140

Lys Trp Asn Glu Leu Leu Glu Glu Ala Leu Lys Val Ile Arg Ser Ile
145                 150                 155                 160

Asp Lys Lys His Thr Ile Ile Gly Thr Ala Glu Trp Gly Gly Ile
                165                 170                 175

Ser Ala Leu Glu Lys Leu Ser Val Pro Lys Trp Glu Lys Asn Ser Ile
            180                 185                 190

Val Thr Ile His Tyr Tyr Asn Pro Phe Lys Phe Thr His Gln Gly Ala
        195                 200                 205

Glu Trp Val Glu Gly Ser Glu Lys Trp Leu Gly Arg Lys Trp Gly Ser
    210                 215                 220

Pro Asp Asp Gln Lys His Leu Ile Glu Glu Phe Asn Phe Ile Glu Glu
225                 230                 235                 240

Trp Ser Lys Lys Asn Lys Arg Pro Ile Tyr Ile Gly Glu Phe Gly Ala
                245                 250                 255

Tyr Arg Lys Ala Asp Leu Glu Ser Arg Ile Lys Trp Thr Ser Phe Val
            260                 265                 270

Val Arg Glu Met Glu Lys Arg Arg Trp Ser Trp Ala Tyr Trp Glu Phe
        275                 280                 285

Cys Ser Gly Phe Gly Val Tyr Asp Thr Leu Arg Lys Thr Trp Asn Asn
    290                 295                 300

Asp Leu Leu Glu Ala Leu Ile Gly Gly Asp Ser Ile Glu
305                 310                 315

<210> SEQ ID NO 7
<211> LENGTH: 317
<212> TYPE: PRT
<213> ORGANISM: Thermotoga maritima
```

<400> SEQUENCE: 7

```
Met Gly Val Asp Pro Phe Glu Arg Asn Lys Ile Leu Gly Arg Gly Ile
1               5                   10                  15

Asn Ile Gly Asn Ala Leu Glu Ala Pro Asn Glu Gly Val Trp Gly Val
            20                  25                  30

Val Ile Lys Asp Glu Phe Phe Asp Ile Ile Lys Glu Ala Gly Phe Ser
        35                  40                  45

His Val Arg Ile Pro Ile Arg Trp Ser Thr His Ala Tyr Ala Phe Pro
    50                  55                  60

Pro Tyr Lys Ile Met Asp Arg Phe Phe Lys Arg Val Asp Glu Val Ile
65                  70                  75                  80

Asn Gly Ala Leu Lys Arg Gly Leu Ala Val Val Phe Asn Ile His His
                85                  90                  95

Tyr Glu Glu Leu Met Asn Asp Pro Glu His Lys Glu Arg Phe Leu
            100                 105                 110

Ala Leu Trp Lys Gln Ile Ala Asp Arg Tyr Lys Asp Tyr Pro Glu Thr
        115                 120                 125

Leu Phe Phe Glu Ile Leu Asn Glu Pro His Gly Asn Leu Thr Pro Glu
    130                 135                 140

Lys Trp Asn Glu Leu Leu Glu Ala Leu Lys Val Ile Arg Ser Ile
145                 150                 155                 160

Asp Lys Lys His Thr Ile Ile Gly Thr Ala Glu Trp Gly Gly Ile
                165                 170                 175

Ser Ala Leu Glu Lys Leu Ser Val Pro Lys Trp Glu Lys Asn Ser Ile
            180                 185                 190

Val Thr Ile His Tyr Tyr Asn Pro Phe Glu Phe Thr His Gln Gly Ala
        195                 200                 205

Glu Trp Val Glu Gly Ser Glu Lys Trp Leu Gly Arg Lys Trp Gly Ser
    210                 215                 220

Pro Asp Asp Gln Lys His Leu Ile Glu Glu Phe Asn Phe Ile Glu Glu
225                 230                 235                 240

Trp Ser Lys Lys Asn Lys Arg Pro Ile Tyr Ile Gly Glu Phe Gly Ala
                245                 250                 255

Tyr Arg Lys Ala Asp Leu Glu Ser Arg Ile Lys Trp Thr Ser Phe Val
            260                 265                 270

Val Arg Glu Met Glu Lys Arg Arg Trp Ser Trp Ala Tyr Trp Glu Phe
        275                 280                 285

Cys Ser Gly Phe Gly Val Tyr Asp Thr Leu Arg Lys Thr Trp Asn Lys
    290                 295                 300

Asp Leu Leu Glu Ala Leu Ile Gly Gly Asp Ser Ile Glu
305                 310                 315
```

<210> SEQ ID NO 8
<211> LENGTH: 317
<212> TYPE: PRT
<213> ORGANISM: Thermotoga maritima

<400> SEQUENCE: 8

```
Met Gly Val Asp Pro Phe Glu Arg Asn Lys Ile Leu Gly Arg Gly Ile
1               5                   10                  15

Asn Ile Gly Asn Ala Leu Glu Ala Pro Asn Glu Gly Asp Trp Gly Val
            20                  25                  30

Val Ile Asn Asp Glu Phe Phe Asp Ile Ile Lys Glu Ala Gly Phe Ser
        35                  40                  45
```

His Val Arg Ile Pro Ile Arg Trp Ser Thr His Ala Tyr Ala Phe Pro
    50                  55                  60

Pro Tyr Lys Ile Met Asp Arg Phe Phe Lys Arg Val Asp Glu Val Ile
65                  70                  75                  80

Asn Gly Ala Leu Lys Arg Gly Leu Ala Val Val Ile Asn Ile His His
                85                  90                  95

Tyr Glu Glu Leu Met Asn Asp Pro Glu His Lys Glu Arg Phe Leu
            100                 105                 110

Ala Leu Trp Lys Gln Ile Ala Asp Arg Tyr Lys Asp Tyr Pro Glu Thr
        115                 120                 125

Leu Phe Phe Glu Ile Leu Asn Glu Pro His Gly Asn Leu Thr Pro Glu
    130                 135                 140

Lys Trp Asn Glu Leu Leu Glu Glu Ala Leu Lys Val Ile Arg Ser Ile
145                 150                 155                 160

Asp Lys Lys His Thr Ile Ile Gly Thr Ala Glu Trp Gly Gly Ile
                165                 170                 175

Ser Ala Leu Glu Lys Leu Ser Val Pro Lys Trp Glu Lys Asn Ser Ile
            180                 185                 190

Val Thr Ile His Tyr Tyr Asn Pro Phe Glu Phe Thr His Gln Gly Ala
        195                 200                 205

Gly Trp Val Glu Gly Ser Glu Lys Trp Leu Gly Arg Lys Trp Gly Ser
    210                 215                 220

Pro Asp Asp Gln Lys His Leu Ile Glu Glu Phe Asn Phe Ile Glu Glu
225                 230                 235                 240

Trp Ser Lys Lys Asn Lys Arg Pro Ile Tyr Ile Gly Glu Phe Gly Thr
                245                 250                 255

Tyr Arg Lys Ala Asp Leu Glu Ser Arg Ile Lys Trp Thr Ser Phe Val
            260                 265                 270

Val Arg Glu Met Glu Lys Arg Arg Trp Ser Trp Ala Tyr Trp Glu Phe
        275                 280                 285

Cys Ser Gly Phe Gly Val Tyr Asp Thr Leu Arg Lys Thr Trp Asn Lys
    290                 295                 300

Asp Leu Leu Glu Ala Leu Ile Gly Gly Asp Ser Ile Glu
305                 310                 315

<210> SEQ ID NO 9
<211> LENGTH: 954
<212> TYPE: DNA
<213> ORGANISM: Thermotoga maritima

<400> SEQUENCE: 9
atgggggttg atccgtttga gcgtaataaa attctgggcc gcggtattaa tatcggcaac      60
gcactggagg ctccgaatga aggtgattgg ggcgtggtta ttaaggatga attcttcgat     120
attatcaaag aagcgggatt tagccatgtg cgtattccga ttcgttggtc gactcatgcc     180
tatgcatttc cgccatacaa aattatggat cgcttttttca aacgtgtgga cgaagttatt     240
aacggtgccc tgaaacgcgg actggccgtt gttattaata tccaccacta tgtagagctg     300
atgaatgatc ctgaagacca taagaacgc tttctggcac tgtggaaaca gattgcggac     360
cgttataaag attatccgga aactctgttt ttcgaaattc tgaacgagcc gcatgggaac     420
ctgacgccgg aaaatggaa tgaactgctg gaagaagctc tgaaagtaat ccgttcgatt     480
gacaagaaac ataccatcat tattggcacc gccgaatggg gtggtatcag tgcactggaa     540
aaactgtcag ttccgaagtg ggagaaaaac tccattgtga cgattcatta ttataacccg     600

```
tttgagttta cccaccaggg ggcagaatgg gtggaaggca gcgaaaaatg gctgggccgt    660
aaatggggta gtcctgatga tcaaaaacac ctgattgaag agtttaactt catcgaagag    720
tggtcaaaaa agaataaacg cccgatttat attggcgagt tcggtgccta tcgcaaagct    780
gatctggaat cgcgtattaa atggacaagt tttgttgtac gtgaaatgga aaagcgccgt    840
tggtcctggg cctattggga attctgtagc ggttttggtg tctacgatac gctgcgcaaa    900
acttggaaca agatctgct ggaagccctg attggcggtg acagtatcga ataa           954
```

<210> SEQ ID NO 10
<211> LENGTH: 954
<212> TYPE: DNA
<213> ORGANISM: Thermotoga maritima

<400> SEQUENCE: 10

```
atgggggttg atccgtttga gcgtaataaa attctgggcc gcggtattaa tatcggcaac    60
gcactggagg ctccgaatga aggtgattgg ggcgtggtta ttaaggatga attcttcaat    120
attatcaaag aagcgggatt tagccatgtg cgtattccga ttcgttggtc gactcatgcc    180
tatgcatttc cgccatacaa aattatggat cgcttttttca aacgtgtgga cgaagttatt    240
aacggtgccc tgaaacgcgg actggccgtt gttattaata tccaccacta tgaagagctg    300
atgaatgatc tgaagaaca taagaacgc tttctggcac tgtggaaaca gattgcggac    360
cgttataaag attatccgga aactctgttt ttcgaaattc tgaacgagcc gcatgggaac    420
ctgacgccgg aaaaatggaa tgaactgctg aagaagctc tgaaagtaat ccgttcgatt    480
gacaagaaac ataccatcat tattggcacc gccgaatggg gtggtatcag tgcactggaa    540
aaactgtcag ttccgaagtg ggagaaaaac tccattgtga cgattcatta ttataacccg    600
tttgagttta cccaccaggg ggcagaatgg gtggaaggca gcgaaaaatg gctgggccgt    660
aaatggggta gtcctgatga tcaaaaacac cggattgaag agtttaactt catcgaagag    720
tggtcaaaaa agaataaacg cccgatttat attggcgagt tcggtgccta tcgcaaagct    780
gatctggaat cgcgtattaa atggacaagt tttgttgtac gtgaaatgga aaagcgccgt    840
tggtcctggg cctattggga attctgtagc ggttttggtg tctacgatac gctgcgcaaa    900
acttggaaca agatctgct ggaagccctg attggcggtg acagtatcga ataa           954
```

<210> SEQ ID NO 11
<211> LENGTH: 954
<212> TYPE: DNA
<213> ORGANISM: Thermotoga maritima

<400> SEQUENCE: 11

```
atgggggttg atccgtttga gcgtaataaa attctgggcc gcggtattaa tatcggcaac    60
gcactggagg ctccgaatga aggtgattgg ggcgtggtta ttaaggatga attcttcgat    120
attatcaaag aagcgggatt tagccatgtg cgtattccga ttcgttggtc gactcatgcc    180
tatgcatttc cgccatacaa aattatggat cgcttttttca aacgtgtgga cgaagttatt    240
aacggtgccc tgaaacgcgg actggccgtt gttattaata tccaccacta tgaagagctg    300
atgaatgatc tgaagaaca taagaacgc tttctggcac tgtggaaaca gattgcggac    360
cgttataaag attatccgga aactctgttt ttcgaaattc tgaacgagcc gcatgggaac    420
ctgacgccgg aaaaatggaa tgaactgctg aagaagctc tgaaagtaat ccgttcgatt    480
gacaagaaac ataccatcat tattggcacc gccgaatggg gtggtatcag tgcactggaa    540
```

```
aaactgtcag ttccgaagtg ggagaaaaac tccattgtga cgattcatta ttataacccg    600
tttgagttta cccaccaggg ggcagaatgg gtggaaggca gcgaaaaatg gctgggccgt    660
aaatggggta gtcctgatga tcaaaaacac ctgattgaag agtttaactt catcgaagag    720
tggtcaaaaa agaataaacg cccgatttat attggcgagt tcggtgccta tcgcaaagct    780
gatctggaat cgcgtattaa atggacaagt tttgttgtac gtgaaatgga aaagcgccgt    840
tggtcctggg cctattggga attctgtagc ggttttggtg tctacgatac gctgcgcaaa    900
acttggaaca aagatctgct gaaagccctg attggcggtg acagtatcga ataa          954
```

<210> SEQ ID NO 12
<211> LENGTH: 954
<212> TYPE: DNA
<213> ORGANISM: Thermotoga maritima

<400> SEQUENCE: 12

```
atgggggttg atccgtttga gcgtaataaa attctgggcc gcggtattaa tatcggcaac     60
gcactggagg ctccgaatga aggtgattgg ggcgtggtta ttaaggatga attcttcgat    120
attatcaaag aagcgggatt tagccatgtg cgtattccga ttcgttggtc gactcatgcc    180
tatgcatttc cgccatacaa aattatggat cgcttttttca aacgtgtgga cgaagttatt    240
aacggtgccc tgaaacgcgg actggccgtt gttattaata tccaccacta tgaagagctg    300
atgaatgatc ctgaagaaca taagaacgc tttctggcac tgtggaaaca gattgcggac    360
cgttataaag attatccgga aactctgttt ttcgaaattc tgaacgagcc gcatgggaac    420
ctgacgccgg aaaatggaa tgaactgctg gaagaagctc tgaatgtaat ccgttcgatt    480
gacaagaaac ataccatcat tattggcacc gccgaatggg gtggtatcag tgcactggaa    540
aaactgtcag ttccgaagtg ggagaaaaac tccattgtga cgattcatta ttataacccg    600
tttgagttta cccaccaggg ggcagaatgg gtggaaggca gcgaaaaatg gctgggccgt    660
aaatggggta gtcctgatga tcaaaaacac ctgattgaag agtttaactt catcgaagag    720
tggtcaaaaa agaataaacg cccgatttat attggcgagt tcggtgccta tcgcaaagct    780
gatctggaat cgcgtattaa atggacaagt tttgttgtac gtgaaatgga aaagcgccgt    840
tggtcctggg cctattggga attctgtagc ggttttggtg tctacgatac gctgcgcaaa    900
acttggaaca aagatctgct ggaagccctg attggcggtg acagtatcga ataa          954
```

<210> SEQ ID NO 13
<211> LENGTH: 954
<212> TYPE: DNA
<213> ORGANISM: Thermotoga maritima

<400> SEQUENCE: 13

```
atgggggttg atccgtttga gcgtaataaa attctgggcc gcggtattaa tatcggcaac     60
gcactggagg ctccgaatga aggtgattgg ggcgtggtta ttaaggatga attcttcgat    120
attatcaaag aagcgggatt tagccatgtg cgtattccga ttcgttggtc gactcatgcc    180
tatgcatttc cgccatacaa aattatggat cgcttttttca aacgtgtgga cgaagttatt    240
aacggtgccc tgaaacgcgg actggccgtt gttattaata tccaccacta tgaagagctg    300
atgaatgatc ctgaagaaca taagaacgc tttctggtac tgtggaaaca gattgcggac    360
cgttataaag attatccgga aactctgttt ttcgaaattc tgaacgagcc gcatgggaac    420
ctgacgccgg aaaatggaa tgaactgctg gaagaagctc tgaaagtaat ccgttcgatt    480
gacaagaaac ataccatcat tattggcacc gccgaatggg gtggtatcag tgcactggaa    540
```

```
aaactgtcag ttccgaagtg ggagaaaaac tccattgtga cgattcatta ttataacccg    600
tttgagttta cccaccaggg ggcagaatgg gtggaaggca cgaaaaatg gctgggccgt    660 aaatggggta gtcctgatga tcaaaaacac ctgattgaag agtttaactt catcgaagag    720
tggtcaaaaa agaataaacg cccgatttat attggcgagt tcggtgccta tcgcaaagct    780
gatctggaat cgcgtattaa atggacaagt tttgttgtac gtgaaatgga aaagcgccgt    840
tggtcctggg cctattggga attctgtagc ggttttggtg tctacgatac gctgcgcaaa    900
acttggaaca aagatctgct ggaagccctg attgcggtg acagtatcga ataa           954
```

<210> SEQ ID NO 14
<211> LENGTH: 954
<212> TYPE: DNA
<213> ORGANISM: Thermotoga maritima

<400> SEQUENCE: 14

```
atgggggttg atccgtttga gcgtaataaa attctgggcc gcggtattaa tatcggcaac    60
gcactggagg ctccgaatga aggtgattgg ggcgtggtta ttaaggatga attcttcgat    120
attatcaaag aagcgggatt tagccatgtg cgtattccga ttcgttggtc gactcatgcc    180
tatgcatttc cgccatacaa aattatggat cgcttttca acgtgtgga cgaagttatt    240 aacggtgccc tgaaacgcgg actggccgtt gttattaata tccaccacta tgaagagctg    300
atgaatgatc ctgaagaaca taagaacgc tttctggcac tgtggaaaca gattgcggac    360
cgttataaag attatccgga aactctgttt ttcgatattc tgaacgagcc gcatgggagc    420
ctgacgccgg aaaaatggaa tgaactgctg aagaagctc tgaaagtaat ccgttcgatt    480
gacaagaaac ataccatcat tattggcacc gccgaatggg gtggtatcag tgcactggaa    540
aaactgtcag ttccgaagtg ggagaaaaac tccattgtga cgattcatta ttataacccg    600
tttaagttta cacaccaggg ggcagaatgg gtggaaggca cgaaaaatg gctgggccgt    660 aaatggggta gtcctgacga tcaaaaacac ctgattgaag agtttaactt catcgaagag    720
tggtcaaaaa agaataaacg cccgatttat attggcgagt tcggtgccta tcgcaaagct    780
gatctggaat cgcggattaa atggacaagt tttgttgtac gtgaaatgga aaagcgccgt    840
tggtcctggg cctattggga attctgtagc ggttttggtg tctacgatac gctgcgcaaa    900
acttggaaca cgatctgct ggaagccctg attgcggtg acagtatcga ataa            954
```

<210> SEQ ID NO 15
<211> LENGTH: 954
<212> TYPE: DNA
<213> ORGANISM: Thermotoga maritima

<400> SEQUENCE: 15

```
atgggggttg atccgtttga gcgtaataaa attctgggcc gcggtattaa tatcggcaac    60
gcactggagg ctccgaatga aggtgtttgg ggtgtggtta ttaaggatga attcttcgat    120
attatcaaag aagcgggatt tagccatgtg cgtattccga ttcgttggtc gactcatgcc    180
tatgcatttc cgccatacaa aattatggat cgcttttca acgtgtgga cgaagttatt    240 aacggtgccc tgaaacgcgg actggccgtt gtttttaata tccaccacta tgaagagctg    300
atgaatgatc ctgaagaaca taagaacgc tttctggcac tgtggaaaca gattgcggac    360
cgttataaag attatccgga aactctgttt ttcgaaattc tgaacgagcc gcatgggaac    420
ctgacgccgg aaaaatggaa tgaactgctg aagaagctc tgaaagtaat ccgttcgatt    480
```

```
gacaagaaac ataccatcat tattggcacc gccgaatggg gtggtatcag tgcactggaa    540
aaactgtcag ttccgaagtg ggagaaaaac tccattgtga cgattcatta ttataacccg    600
tttgagttta cccaccaggg ggcagaatgg gtggaaggca gcgaaaaatg gctgggccgt    660
aaatggggta gtcctgatga tcaaaaacac ctgattgaag agtttaactt catcgaagag    720
tggtcaaaaa agaataaacg cccgatttat attggcgagt cggtgcccta tcgcaaagct    780
gatctggaat cgcgtattaa atggacaagt tttgttgtac gtgaaatgga aaagcgccgt    840
tggtcctggg cctattggga attctgtagc ggttttggtg tctacgatac gctgcgcaaa    900
acttggaaca agatctgct ggaagccctg attggcggtg acagtatcga ataa           954

<210> SEQ ID NO 16
<211> LENGTH: 954
<212> TYPE: DNA
<213> ORGANISM: Thermotoga maritima

<400> SEQUENCE: 16
atgggggttg atccgtttga gcgtaataaa attctgggcc gcggtattaa tatcggcaac     60
gcactggagg ctccgaatga aggtgattgg ggtgtggtta ttaatgatga attcttcgat    120
attatcaaag aagcgggatt tagccatgtg cgtattccga ttcgttggtc gactcatgcc    180
tatgcatttc cgccatacaa aattatggat cgcttttttca aacgtgtgga cgaagttatt    240
aacggtgccc tgaaacgcgg actggccgtt gttattaata tccaccacta tgaagagctg    300
atgaatgatc ctgaagaaca taagaacgc tttctggcac tgtggaaaca gattgcggac    360
cgttataaag attatccgga aactctgttt ttcgaaattc tgaacgagcc gcatgggaac    420
ctgacgccgg aaaatggaa tgaactgctg gaagaagctc tgaaagtaat ccgttcgatt    480
gacaagaaac ataccatcat tattggcacc gccgaatggg gtggtatcag tgcactggaa    540
aaactgtcag ttccgaagtg ggagaaaaac tccattgtga cgattcatta ttataacccg    600
tttgagttta cccaccaggg ggcaggatgg gtggaaggca gcgaaaaatg gctgggccgt    660
aaatggggta gtcctgatga tcaaaaacac ctgattgaag agtttaactt catcgaagag    720
tggtcaaaaa agaataaacg cccgatttat attggcgagt cggtaccta tcgcaaagct    780 gatctggaat cgcgtattaa atggacaagt tttgttgtac gtgaaatgga aaagcgccgt    840
tggtcctggg cctattggga attctgtagc ggttttggtg tctacgatac gctgcgcaaa    900
acttggaaca agatctgct ggaagccctg attggcggtg acagtatcga ataa           954

<210> SEQ ID NO 17
<211> LENGTH: 954
<212> TYPE: DNA
<213> ORGANISM: Thermotoga maritima

<400> SEQUENCE: 17
atgggggttg atccgtttga gcgtaataaa attctgggcc gcggtattaa tatcggcaac     60
gcactggagg ctccgaatga aggtgattgg ggcgtggtta ttaaggatga attcttcgat    120
attatcaaag aagcgggatt tagccatgtg cgtattccga ttcgttggtc gactcatgcc    180
tatgcatttc cgccatacaa aattatggat cgcttttttca aacgtgtgga cgaagttatt    240
aacggtgccc tgaaacgcgg actggccgtt gttattaata tccaccacta tgaagagctg    300
atgaatgatc ctgaagaaca taagaacgc tttctggcac tgtggaaaca gattgcggac    360
cgttataaag attatccgga aactctgttt ttcgaaattc tgaacgagcc gcatgggaac    420
ctgacgccgg aaaatggaa tgaactgctg gaagaagctc tgaaagtaat ccgttcgatt    480
```

-continued

```
gacaagaaac ataccatcat tattggcacc gccgaatggg gtggtatcag agcactggaa    540
aaactgtcag ttccgaagtg ggagaaaaac tccattgtga cgattcatta ttataacccg    600
tttgagttta cccaccaggg ggcagaatgg gtggaaggca gcgaaaaatg gctgggccgt    660
aaatggggta gtcctgatga tcaaaaacac ctgattgaag agtttaactt catcgaagag    720
tggtcaaaaa agaataaacg cccgatttat attggcgagt cggtgcctta tcgcaaagct    780
gatctggaat cgcgtattaa atggacaagt tttgttgtac gtgaaatgga aaagcgccgt    840
tggtcctggg cctattggga attctgtagc ggttttggtg tctacgatac gctgcgcaaa    900
acttggaaca agatctgct ggaagccctg attggcggtg acagtatcga ataa          954
```

<210> SEQ ID NO 18
<211> LENGTH: 30
<212> TYPE: DNA
<213> ORGANISM: Artificial Sequence
<220> FEATURE:
<223> OTHER INFORMATION: Synethetic primer used for cloning Thermotoga
      maritima Cel5A

<400> SEQUENCE: 18

```
gacgacgaca agatgggggt tgatccgttt                                      30
```

<210> SEQ ID NO 19
<211> LENGTH: 35
<212> TYPE: DNA
<213> ORGANISM: Artificial Sequence
<220> FEATURE:
<223> OTHER INFORMATION: Synethetic primer used for cloning Thermotoga
      maritima Cel5A

<400> SEQUENCE: 19

```
gaggagaagc ccggttattc gatactgtca ccgcc                                35
```

<210> SEQ ID NO 20
<211> LENGTH: 317
<212> TYPE: PRT
<213> ORGANISM: Thermotoga maritima

<400> SEQUENCE: 20

```
Met Gly Val Asp Pro Phe Glu Arg Asn Lys Ile Leu Gly Arg Gly Ile
1               5                   10                  15

Asn Ile Gly Asn Ala Leu Glu Ala Pro Asn Glu Gly Asp Trp Gly Val
            20                  25                  30

Val Ile Lys Asp Glu Phe Phe Asp Ile Ile Lys Glu Ala Gly Phe Ser
        35                  40                  45

His Val Arg Ile Pro Ile Arg Trp Ser Thr His Ala Tyr Ala Phe Pro
    50                  55                  60

Pro Tyr Lys Ile Met Asp Arg Phe Phe Lys Arg Val Asp Glu Val Ile
65                  70                  75                  80

Asn Gly Ala Leu Lys Arg Gly Leu Ala Val Val Ile Asn Ile His His
                85                  90                  95

Tyr Glu Glu Leu Met Asn Asp Pro Glu Glu His Lys Glu Arg Phe Leu
            100                 105                 110

Ala Leu Trp Lys Gln Ile Ala Asp Arg Tyr Lys Asp Tyr Pro Glu Thr
        115                 120                 125

Leu Phe Phe Glu Ile Leu Asn Glu Pro His Gly Asn Leu Thr Pro Glu
    130                 135                 140

Lys Trp Asn Glu Leu Leu Glu Glu Ala Leu Lys Val Ile Arg Ser Ile
```

```
                145                 150                 155                 160
Asp Lys Lys His Thr Ile Ile Ile Gly Thr Ala Glu Trp Gly Gly Ile
                    165                 170                 175

Ser Ala Leu Glu Lys Leu Ser Val Pro Lys Trp Glu Lys Asn Ser Ile
                180                 185                 190

Val Thr Ile His Tyr Tyr Asn Pro Phe Glu Phe Thr His Gln Gly Ala
            195                 200                 205

Glu Trp Val Glu Gly Ser Glu Lys Trp Leu Gly Arg Lys Trp Gly Ser
        210                 215                 220

Pro Asp Asp Gln Lys His Leu Ile Glu Glu Phe Asn Phe Ile Glu Glu
225                 230                 235                 240

Trp Ser Lys Lys Asn Lys Arg Pro Ile Tyr Ile Gly Glu Phe Gly Ala
                245                 250                 255

Tyr Arg Lys Ala Asp Leu Glu Ser Arg Ile Lys Trp Thr Ser Phe Val
                260                 265                 270

Val Arg Glu Met Glu Lys Arg Arg Trp Ser Trp Ala Tyr Trp Glu Phe
            275                 280                 285

Cys Ser Gly Phe Gly Val Tyr Asp Thr Leu Arg Lys Thr Trp Asn Lys
        290                 295                 300

Asp Leu Leu Glu Ala Leu Ile Gly Gly Asp Ser Ile Glu
305                 310                 315

<210> SEQ ID NO 21
<211> LENGTH: 458
<212> TYPE: PRT
<213> ORGANISM: Pyrococcus horikoshii

<400> SEQUENCE: 21

Met Glu Gly Asn Thr Ile Leu Lys Ile Val Leu Ile Cys Thr Ile Leu
1               5                   10                  15

Ala Gly Leu Phe Gly Gln Val Val Pro Val Tyr Ala Glu Asn Thr Thr
            20                  25                  30

Tyr Gln Thr Pro Thr Gly Ile Tyr Tyr Glu Val Arg Gly Asp Thr Ile
        35                  40                  45

Tyr Met Ile Asn Val Thr Ser Gly Glu Glu Thr Pro Ile His Leu Phe
    50                  55                  60

Gly Val Asn Trp Phe Gly Phe Glu Thr Pro Asn His Val Val His Gly
65                  70                  75                  80

Leu Trp Lys Arg Asn Trp Glu Asp Met Leu Leu Gln Ile Lys Ser Leu
                85                  90                  95

Gly Phe Asn Ala Ile Arg Leu Pro Phe Cys Thr Glu Ser Val Lys Pro
            100                 105                 110

Gly Thr Gln Pro Ile Gly Ile Asp Tyr Ser Lys Asn Pro Asp Leu Arg
        115                 120                 125

Gly Leu Asp Ser Leu Gln Ile Met Glu Lys Ile Ile Lys Lys Ala Gly
    130                 135                 140

Asp Leu Gly Ile Phe Val Leu Leu Asp Tyr His Arg Ile Gly Cys Thr
145                 150                 155                 160

His Ile Glu Pro Leu Trp Tyr Thr Glu Asp Phe Ser Glu Glu Asp Phe
                165                 170                 175

Ile Asn Thr Trp Ile Glu Val Ala Lys Arg Phe Gly Lys Tyr Trp Asn
            180                 185                 190

Val Ile Gly Ala Asp Leu Lys Asn Glu Pro His Ser Val Thr Ser Pro
        195                 200                 205
```

```
Pro Ala Ala Tyr Thr Asp Gly Thr Gly Ala Thr Trp Gly Met Gly Asn
    210                 215                 220

Pro Ala Thr Asp Trp Asn Leu Ala Ala Glu Arg Ile Gly Lys Ala Ile
225                 230                 235                 240

Leu Lys Val Ala Pro His Trp Leu Ile Phe Val Glu Gly Thr Gln Phe
            245                 250                 255

Thr Asn Pro Lys Thr Asp Ser Ser Tyr Lys Trp Gly Tyr Asn Ala Trp
        260                 265                 270

Trp Gly Gly Asn Leu Met Ala Val Lys Asp Tyr Pro Val Asn Leu Pro
    275                 280                 285

Arg Asn Lys Leu Val Tyr Ser Pro His Val Tyr Gly Pro Asp Val Tyr
290                 295                 300

Asn Gln Pro Tyr Phe Gly Pro Ala Lys Gly Phe Pro Asp Asn Leu Pro
305                 310                 315                 320

Asp Ile Trp Tyr His His Phe Gly Tyr Val Lys Leu Glu Leu Gly Tyr
            325                 330                 335

Ser Val Val Ile Gly Glu Phe Gly Lys Tyr Gly His Gly Gly Asp
        340                 345                 350

Pro Arg Asp Val Ile Trp Gln Asn Lys Leu Val Asp Trp Met Ile Glu
    355                 360                 365

Asn Lys Phe Cys Asp Phe Phe Tyr Trp Ser Trp Asn Pro Asp Ser Gly
370                 375                 380

Asp Thr Gly Gly Ile Leu Gln Asp Trp Thr Thr Ile Trp Glu Asp
385                 390                 395                 400

Lys Tyr Asn Asn Leu Lys Arg Leu Met Asp Ser Cys Ser Lys Ser Ser
            405                 410                 415

Ser Ser Thr Gln Ser Val Ile Arg Ser Thr Thr Pro Thr Lys Ser Asn
        420                 425                 430

Thr Ser Lys Lys Ile Cys Gly Pro Ala Ile Leu Ile Leu Ala Val
    435                 440                 445

Phe Ser Leu Leu Leu Arg Arg Ala Pro Arg
450                 455

<210> SEQ ID NO 22
<211> LENGTH: 317
<212> TYPE: PRT
<213> ORGANISM: Thermotoga maritima

<400> SEQUENCE: 22

Met Gly Val Asp Pro Phe Glu Arg Asn Lys Ile Leu Gly Arg Gly Ile
1               5                   10                  15

Asn Ile Gly Asn Ala Leu Glu Ala Pro Asn Glu Gly Asp Trp Gly Val
            20                  25                  30

Val Ile Lys Asp Glu Phe Phe Asp Ile Ile Lys Glu Ala Gly Phe Ser
        35                  40                  45

His Val Arg Ile Pro Ile Arg Trp Ser Thr His Ala Tyr Ala Phe Pro
    50                  55                  60

Pro Tyr Lys Ile Met Asp Arg Phe Phe Lys Arg Val Asp Glu Val Ile
65                  70                  75                  80

Asn Gly Ala Leu Lys Arg Gly Leu Ala Val Val Ile Asn Ile His His
            85                  90                  95

Tyr Glu Glu Leu Met Asn Asp Pro Glu Glu His Lys Glu Arg Phe Leu
        100                 105                 110

Ala Leu Trp Lys Gln Ile Ala Asp Arg Tyr Lys Asp Tyr Pro Glu Thr
    115                 120                 125
```

```
Leu Phe Phe Glu Ile Leu Asn Glu Pro His Gly Asn Leu Thr Pro Glu
    130             135             140

Lys Trp Asn Glu Leu Leu Glu Glu Ala Leu Lys Val Ile Arg Ser Ile
145             150             155             160

Asp Lys Lys His Thr Ile Ile Ile Gly Thr Ala Glu Trp Gly Gly Ile
            165             170             175

Arg Ala Leu Glu Lys Leu Ser Val Pro Lys Trp Glu Lys Asn Ser Ile
            180             185             190

Val Thr Ile His Tyr Tyr Asn Pro Phe Glu Phe Thr His Gln Gly Ala
            195             200             205

Glu Trp Val Glu Gly Ser Glu Lys Trp Leu Gly Arg Lys Trp Gly Ser
    210             215             220

Pro Asp Asp Gln Lys His Leu Ile Glu Glu Phe Asn Phe Ile Glu Glu
225             230             235             240

Trp Ser Lys Lys Asn Lys Arg Pro Ile Tyr Ile Gly Glu Phe Gly Ala
            245             250             255

Tyr Arg Lys Ala Asp Leu Glu Ser Arg Ile Lys Trp Thr Ser Phe Val
            260             265             270

Val Arg Glu Met Glu Lys Arg Arg Trp Ser Trp Ala Tyr Trp Glu Phe
    275             280             285

Cys Ser Gly Phe Gly Val Tyr Asp Thr Leu Arg Lys Thr Trp Asn Lys
    290             295             300

Asp Leu Leu Glu Ala Leu Ile Gly Gly Asp Ser Ile Glu
305             310             315
```

THERMOSTABLE CELLULASES, AND MUTANTS THEREOF, CAPABLE OF HYDROLYZING CELLULOSE IN IONIC LIQUID

RELATED PATENT APPLICATIONS

The application is a U.S. National Stage entry of International Application No. PCT/US2010/032320, filed Apr. 23, 2010, and claims priority to U.S. Provisional Patent Application Ser. No. 61/172,653, filed Apr. 24, 2009, and 61/172,668, filed Apr. 24, 2009, each of which are herein incorporated by reference in its their entireties.

STATEMENT OF GOVERNMENTAL SUPPORT

The invention was made with government support under Contract No. DE-AC02-05CH11231 awarded by the U.S. Department of Energy. The government has certain rights in the invention.

REFERENCE TO A "SEQUENCE LISTING" SUBMITTED AS AN ASCII TEXT FILE

The Sequence Listing written in file SEQTXT_77429-822507_009900US.TXT, created on Mar. 9, 2015; 44,659 bytes, machine format IBM-PC, MS-Windows operating system, is hereby incorporated by reference.

FIELD OF THE INVENTION

The present invention is in the field of saccharification of biomass.

BACKGROUND OF THE INVENTION

Biomass pretreatment for efficient conversion to sugars remains one of the most challenging obstacles to the design of an economically viable bio-refinery for liquid fuel production. Several pretreatment and biomass fermentation fractionation (separation of carbohydrate and lignin components) technologies exist or under consideration, these include dilute acid, solvo-thermal, hydrothermal, ammonia fiber explosion, and others.

Enzymatic hydrolysis is the rate limiting step in the fermentation of biomass to sugars. The main barrier is the highly crystalline structure of cellulose that limits accessibility to enzyme adsorption sites and slows the hydrolysis of cellulose to sugars in aqueous media. To increase enzyme accessibility, a combination of high temperature and extremes of pH are used during common pretreatment steps like dilute acid or ammonia fiber explosion.

A promising new candidate technology for biomass fractionation is ionic liquid pretreatment. In an ionic liquid pretreatment process, biomass is dissolved in an ionic liquid, and carbohydrates such as hemicellulose and cellulose are precipitated on the addition of an anti-solvent such as water. The regenerated cellulose possesses an amorphous structure that is especially amenable to enzymatic saccharification and may contain little or no inhibitory components for subsequent processing to ethanol or other biofuels. The lignin remains in solution and can be removed from the ionic liquid by other thermal, liquid extraction, or other methods that have not been fully described. The relatively expensive ionic liquid is recovered and recycled into the process.

Ionic liquid pretreatment method has been used to convert lignocellulose to sugars, since current pretreatment approaches are energy and cost intensive. Methods are being developed for the conversion of crystalline cellulose to sugars with improvements in yield and rate of sugar production using a simultaneous pretreatment and saccharification using a one step ionic liquid. The pretreatment step has been developed with the use of ionic liquid to break down crystalline cellulosic biomass. While the second step of hydrolyzing cellulose to sugars would require separation of cellulose from ionic liquid, an enzyme that is compatible with the concentrations of ionic liquid used in pretreatment step would eliminate the need for this step, thereby improving yield and reducing time and cost.

Endoglucanases are hydrolytic enzymes that catalyze the endo cleavage of cellulose polymer to smaller units like cellobiose and are used as a starting point in the hydrolysis of cellulosic polymers to simpler sugars like glucose. While the enzymes, i.e. biocatalysts, discovered in nature have a distinct and characteristic activity, the activity of these natural variants is generally low in industrial application that require high activity to compete with chemical catalysis. Secondly, green chemistry requires the use of products that are biodegradable and enzymes are biodegradable catalysts that can be used in industrial hydrolysis of cellulose to sugars.

Currently, people use techniques that are based on treating the biomass with a combination of high temperature and acid or base, or chemicals like lime. These methods have two distinct disadvantages—first, the industrial enzymes are used to break down cellulose are not compatible with such harsh methods making a single pretreatment and saccharification method impossible. Secondly, these methods create unwanted byproducts that interfere with the downstream hydrolysis and fuel production steps.

SUMMARY OF THE INVENTION

The present invention provides for a composition comprising an ionic liquid and a thermostable cellulase. In some embodiments, the composition further comprises a cellulose, wherein the thermostable cellulase is capable of hydrolyzing the cellulose. In some embodiments, the composition comprises a pretreatment biomass.

The present invention provides for a method of hydrolyzing a cellulose, comprising: (a) providing a composition comprising a solution comprising an ionic liquid and a cellulose, and (b) introducing a thermostable cellulase to the solution, such that the cellulose is hydrolyzed by the cellulase. In some embodiments, the solution comprises a pretreatment biomass.

The present invention provides for a method for converting of the carbohydrates of lignocellulose to sugars with improvements in yield and rate of sugar production has been developed by using thermostable cellulase that are compatible with ionic liquid (IL) pretreatment. These enzymes substantially improve the yield of saccharification of cellulose compared to commercially available enzymes and are active in the presence of up to 4% of a suitable IL, such as 1-ethyl-3-methyl-imidazolium acetate (EMIM Acetate).

In some embodiments, the pretreatment biomass is a pretreatment cellulose biomass, pretreatment hemicellulose biomass, pretreatment lingo-cellulose biomass, or a mixture thereof.

The present invention provides for a method for converting lignocellulosic biomass to sugars for the production of biofuels. Methods for the pretreatment of biomass and the downstream enzymatic hydrolysis that is required to breakdown the long polymers of cellulose to simpler sugars for biofuels production.

The present invention provides for a method that is compatible with biomass pretreatment with IL.

The hydrolysis of cellulose, by suitable thermostable enzymes, is unaffected even in the presence of 4% IL in the reaction pot or solution, thus making the enzyme compatible with the pretreatment step. This method substantially improves the efficiency (in terms of yield and reaction rates) of saccharification of cellulose and opens up the possibility of one pot saccharification of lignocellulosic biomass.

The present invention provides for a method for using ionic liquids (IL), a new class of environment friendly, non-volatile solvents, in the pretreatment of cellulosic biomass together with a thermostable cellulase. Such thermostable cellulases include extremophilic enzymes that are stable and suitable for use with an IL, such as 1-ethyl-3-methylimidazolium acetate (EMIM acetate or [C2mim][OAc]).

The present invention provides for a *Thermatoga maritima* thermostable cellulase mutant with increased cellulase activity. The thermostable cellulase mutant comprises an amino acid sequence having at least 70% identity as compared to the amino acid sequence of wild-type cellulase of *Thermatoga maritima* MSB8 (encoded by the cel5A gene), wherein the amino acid sequence of the thermostable cellulase mutant comprises one or more amino acid residues are altered as compared to the amino acid sequence of the wild-type cellulase. The thermostable cellulase mutant has a cellulase activity higher than that of the wild-type *T. maritima* thermostable cellulase.

The present invention provides for a nucleic acid encoding any of the *T. maritima* thermostable cellulase mutants of the present invention. In some embodiments of the invention, the nucleic acid is recombinant or isolated or purified.

The present invention provides for a host cell comprising a nucleic acid of the present invention.

The present invention provides for a method for producing a thermostable cellulase mutant of the present invention comprising: providing a host cell capable of expressing the thermostable cellulase mutant, culturing the host cell in a culture medium under conditions whereby the thermostable cellulase mutant is produced, optionally isolating the thermostable cellulase mutant from the host cell and/or the culture medium, and optionally contacting the thermostable cellulase mutant and a cellulose, whereby the cellulose is hydrolyzed by the thermostable cellulase mutant.

In some embodiments of the invention, the providing step comprises: introducing an expression vector capable of expressing the thermostable cellulase mutant in the host cell into the host cell, and optionally constructing the expression vector encoding a promoter operatively linked to a nucleic acid encoding the thermostable cellulase mutant, wherein the constructing step precedes the introducing step.

The present invention provides for a composition comprising the *T. maritima* thermostable cellulase mutant of the present invention. In some embodiments, the thermostable cellulase mutant is isolated or purified.

In some embodiments of the invention, the composition further comprises an ionic liquid (IL). In some embodiments of the invention, the composition further comprises a cellulose, wherein the thermostable cellulase mutant is capable of hydrolyzing the cellulose. In some embodiments of the invention, the composition further comprises an ionic liquid and a cellulose, wherein the thermostable cellulase is capable of hydrolyzing the cellulose. In some embodiments of the invention, the composition comprises a pretreatment biomass.

The present invention provides for a method of hydrolyzing a cellulose, comprising: providing a composition comprising a solution comprising an ionic liquid, a cellulose, and a thermostable cellulase mutant of the present invention to the solution, such that the cellulose is hydrolyzed by the thermostable cellulase mutant. In some embodiments of the invention, the solution comprises a pretreatment biomass.

The present invention provides for a method for converting of the carbohydrates of lignocellulose to sugars with improvements in yield and rate of sugar production has been developed by using the thermostable cellulase mutant of the invention. In some embodiments of the invention, the thermostable cellulase mutant is compatible with ionic liquid (IL). In some embodiments, the thermostable cellulase mutant is introduced to a pretreatment biomass comprising a pretreatment cellulose biomass, pretreatment hemicellulose biomass, pretreatment lingo-cellulose biomass, or a mixture thereof.

The present invention provides for a method for converting a lignocellulosic biomass to sugars for the production of biofuels using the thermostable cellulase mutant.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1:
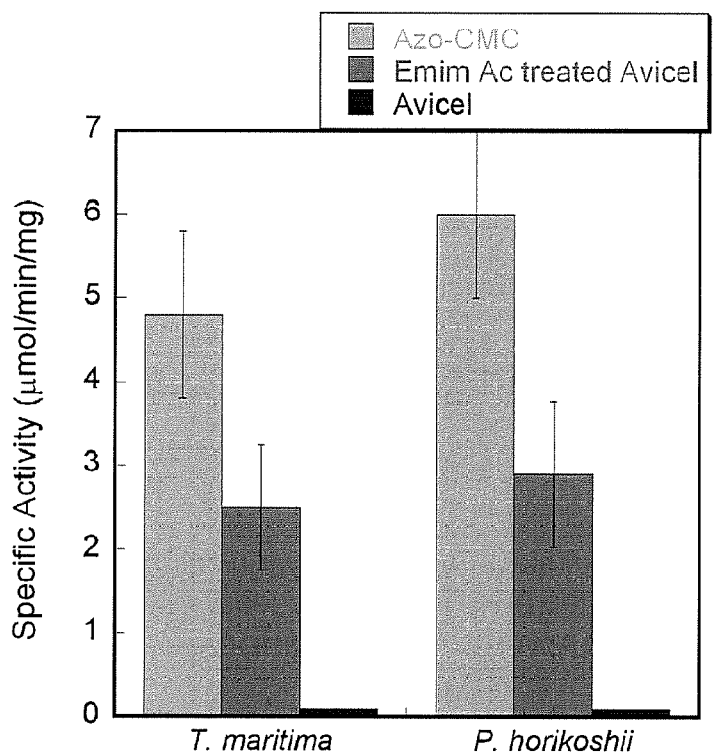
FIG. 1 shows the specific activities of the endoglucanase enzyme of *T. maritima* and *P. horikoshii*.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "IL" includes a single IL compound as well as a plurality of IL compounds, either the same (e.g., the same molecule) or different.

In this specification and in the claims that follow, reference will be made to a number of terms that shall be defined to have the following meanings:

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Particular expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "host cell" refers to a living biological cell that can be transformed via insertion of an expression vector. Thus, a host cell as described herein may be a prokaryotic organism (e.g., an organism of the kingdom Eubacteria) or a eukaryotic cell.

The term "isolated" refers to material that is substantially or essentially free of components that normally accompany it in its native state.

As used herein, the terms "nucleic acid", "nucleotide" and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing nonnucleotidic backbones, provided that the polymers contain nucleobases in a configuration that allows for base pairing and base stacking, as found in DNA and RNA.

The term "operably linked" refers to a functional linkage between a nucleic acid expression control sequence (such as a promoter) and a second nucleic acid sequence, wherein the expression control sequence directs transcription of the nucleic acid corresponding to the second sequence.

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The term "transduce" as used herein refers to the transfer of a sequence of nucleic acids into a host cell. Only when the sequence of nucleic acids becomes stably replicated by the host cell does the host cell become "transformed." As will be appreciated by those of ordinary skill in the art, "transformation" may take place either by incorporation of the sequence of nucleic acids into the cellular genome, i.e., chromosomal integration, or by extrachromosomal integration. In contrast, an expression vector, e.g., a virus, is "infective" when it transduces a host microorganism, replicates, and (without the benefit of any complementary virus or vector) spreads progeny expression vectors, e.g., viruses, of the same type as the original transducing expression vector to other host cells, wherein the progeny expression vectors possess the same ability to reproduce.

Biomass Pretreatment

Biomass or cellulose pretreatment is described in Hermanutz, et al. (2008) *Macromol. Symp.* 262:23-27, which is incorporated by reference.

Ionic Liquid (IL)

The IL used in the present invention can be any IL suitable for pretreatment of biomass and for the hydrolysis of cellulose by thermostable cellulase. Suitable IL are taught in ChemFiles (2006) 6(9) (which are commercially available from Sigma-Aldrich; Milwaukee, Wis.). Such suitable IL include, 1-alkyl-3-alkylimidazolium alkanate, 1-alkyl-3-alkylimidazolium alkylsulfate, 1-alkyl-3-alkylimidazolium methylsulfonate, 1-alkyl-3-alkylimidazolium hydrogensulfate, 1-alkyl-3-alkylimidazolium thiocyanate, and 1-alkyl-3-alkylimidazolium halide, wherein an "alkyl" is an alkyl group comprising from 1 to 10 carbon atoms, and an "alkanate" is an alkanate comprising from 1 to 10 carbon atoms. In some embodiments, the "alkyl" is an alkyl group comprising from 1 to 4 carbon atoms. In some embodiments, the "alkyl" is an methyl group, ethyl group or butyl group. In some embodiments, the "alkanate" is an alkanate comprising from 1 to 4 carbon atoms. In some embodiments, the "alkanate" is an acetate. In some embodiments, the halide is chloride.

Such suitable IL include, but are limited to, 1-ethyl-3-methylimidazolium acetate (EMIN Acetate), 1-ethyl-3-methylimidazolium chloride (EMIN Cl), 1-ethyl-3-methylimidazolium hydrogensulfate (EMIM $HOS_{O3}$), 1-ethyl-3-methylimidazolium methylsulfate (EMIM $MeOS_{O3}$), 1-ethyl-3-methylimidazolium ethylsulfate (EMIM $EtOS_{O3}$), 1-ethyl-3-methylimidazolium methanesulfonate (EMIM $MeS_{O3}$), 1-ethyl-3-methylimidazolium tetrachloroaluminate (EMIM $AIC_{14}$), 1-ethyl-3-methylimidazolium thiocyanate (EMIM SCN), 1-butyl-3-methylimidazolium acetate (BMIM Acetate), 1-butyl-3-methylimidazolium chloride (BMIM Cl), 1-butyl-3-methylimidazolium hydrogensulfate (BMIM $HOS_{O3}$), 1-butyl-3-methylimidazolium methanesulfonate (BMIM $MeS_{O3}$), 1-butyl-3-methylimidazolium methylsulfate (BMIM $MeOS_{O3}$), 1-butyl-3-methylimidazolium tetrachloroaluminate (BMIM $AIC_{14}$), 1-butyl-3-methylimidazolium thiocyanate (BMIM SCN), 1-ethyl-2,3-dimethylimidazolium ethylsulfate (EDIM $EtOS_{O3}$), Tris(2-hydroxyethyl)methylammonium methylsulfate (MTEOA $MeOS_{O3}$), 1-methylimidazolium chloride (MIM Cl), 1-methylimidazolium hydrogensulfate (MIM $HOS_{O3}$), 1,2,4-trimethylpyrazolium methylsulfate, tributylmethylammonium methylsulfate, choline acetate, choline salicylate, and the like. The ionic liquid can comprises one or a mixture of the compounds. Further ILs are taught in U.S. Pat. No. 6,177,575.

The ionic liquid is of a concentration of more than 0% of the solution. In some embodiments, the concentration of IL in the solution is equal to or more than 1%, equal to or more than 2%, equal to or more than 3%, equal to or more than 5%, equal to or more than 10%, equal to or more than 15%, or equal to or more than 20%. In some embodiments, the concentration of IL in the solution is equal to or less than 1%, equal to or less than 2%, equal to or less than 3%, equal to or less than 5%, equal to or less than 10%, equal to or less than 15%, or equal to or less than 20%.

Thermostable Cellulases

The thermostable cellulases suitable for use in the present invention, include are any thermostable cellulase from the genus *Anaerocellu, Bacillus, Rhodothermus, Thermotoga, Sulfolobus*, or *Pyrococcus*. Suitable species of the genus *Anaerocellu* include *A. thermophilum*. Suitable species of the genus *Bacillus* include *B. subtilus*. Suitable species of the genus *Rhodothermus* include *R. marinus*. Suitable species of the genus *Thermatoga* include *T. maritima, T. neapoltana*, and *T. subterranea*. Suitable species of the genus *Sulfolobus* include *S. solfataricus* MT4, *S. acidocaldarius*, and *S. shibatae*. Suitable species of the genus *Pyrococcus* include *P. horikoshii, P. horicoshi, P. woesei*, and *P. furiosus*. In some embodiments, the thermostable cellulase is a cellulase obtained from or native to a hyperthermophilic microorganism, an extremophilic microorganism, or thermophilic microorganism. In some embodiments, the thermostable cellulase is a thermophilic cellulase. In some embodiments, the thermostable cellulase is a thermostable endoglucanase or a thermophilic endoglucanase. Some of the suitable thermostable cellulases are listed in Table 1. Suitable thermostable cellulases include any thermostable cellulases mutants of the present invention.

TABLE 1

Source microorganisms and properties of thermostable cellulases.

| Organism | Enzyme properties | | References |
|---|---|---|---|
| | Optimal temperature (° C.) | Optimal pH | |
| *Anaerocellu thermophilum* | 85-90 | 5.0-6.6 | Zverlov et al. (1998) |
| *Bacillus subtilis* | 65-70 | 5.0-6.5 | Mawadza et al. (2000) |
| *Pyrococcus furiosus* | 102-105 | — | Kengen et al. (1993) |
| *Pyrococcus horicoshi* | 97 | — | Ando et al. (2002) |
| *Rhodothermus marinus* | 95 | 6.5-8.0 | Hreggvidsson et al. (1996) |
| *Thermotoga maritema* MSB8 | 95 | 6.0-7.0 | Bronnemeier et al. (1995) |
| *Thermotoga neapoliana* (EndocellulaseA) | 95 | 6.0 | Bok et al. (1998) |
| *Thermotoga neapoliana* (EndocellulaseB) | 106 | 6.0-6.6 | Bok et al. (1998) |

Zverlov, V., Riedel, K. and Bronnenmeier, K., 1998. Properties and gene structure of a bifunctional cellulytic enzyme (CelA) from the extreme thermophile *Anaerocellum thermophilum* with separate glycosyl hydrolase family 9 and 48 catalytic domains. *Microbiology* 144, pp. 457-465.

Mawadza, C., Hatti-Kaul, R., Zvauya, R. and Mattiasson, B., 2000. Purification and characterization of cellulases produced by two *Bacillus* strains. *J. Biotechnol.* 83, pp. 177-187.

Kengen, S., Luesink, E., Stams, A. and Zehnder, A., 1993. Purification and characterization of an extremely thermostable β-glucosidase from the hyperthermophilic archaeon *Pyrococccus furiosus*. *Eur. J. Biochem.* 213, pp. 305-312.

Ando, S., Ishida, H., Kosugi, Y. and Ishikawa, K., 2002. Hyperthermostable endoglucanase from *Pyrococcus horikoshi*. *Appl. Environ. Microbiol.* 68, pp. 430-433.

Hreggvidsson, G. O., Kaiste, E., Holst, O., Eggertsson, G., Palsdottir, A. and Kristjansson, J. K., 1996. An extremely thermostable cellulase from the thermophilic *eubacterium Rhodothermus marinus*. *Appl. Environ. Microbiol.* 62, pp. 3047-3049.

Bronnenmeier, K., Kern, A., Libel, W. and Staudenbauer, W., 1995. Purification of *Thermatoga maritema* enzymes for the degradation of cellulose materials. *Appl. Environ. Microbiol.* 61, pp. 1399-1407.

Bok, J., Goers, S, and Eveleigh, D., 1994. Cellulase and xylanase systems of *Thermatoga neapolitana*. *ACS Symp. Ser.* 566, pp. 54-65.

Bok, J., Dienesh, A., Yernool, D. and Eveleigh, D., 1998. Purification, characterization and molecular analysis of thermostable cellulases CelA and CelB from *Thermatoga neapolitana*. *Appl. Environ. Microbiol.* 64, pp. 4774-4781.

The above references are incorporated by reference as though each is individually and specifically incorporated by reference.

A thermostable cellulase is a cellulase, or a homologous enzyme thereof, that has an enzymatic activity for hydrolyzing cellulose, hemicelluloses, or lignocelluloses that has an optimal temperature that is equal to or more than 65° C. A thermostable cellulase includes, but is not limited to, a endoglucanase, exoglucanase, or β-1,4-D-glucosidase, or a homologous enzyme thereof, that has an optimal temperature that is equal to or more than 65° C. In some embodiments, optimal temperature is equal to or more than 85° C. In some embodiments, optimal temperature is equal to or more than 95° C.

A homologous cellulase is an enzyme that has a polypeptide sequence that is at least 70%, 75%, 80%, 85%, 90%, 95% or 99% identical to any one of the enzymes described in this specification or in an incorporated reference. The homologous enzyme retains amino acids residues that are recognized as conserved for the enzyme. The homologous enzyme may have non-conserved amino acid residues replaced or found to be of a different amino acid, or amino acid(s) inserted or deleted, but which does not affect or has insignificant effect on the enzymatic activity of the homologous enzyme. The homologous enzyme has an enzymatic activity that is identical or essentially identical to the enzymatic activity any one of the enzymes described in this specification or in an incorporated reference. The homologous enzyme may be found in nature or be an engineered mutant thereof.

The present invention addresses two significant challenges in biomass processing-IL have shown to be very effective in "solubilizing" lignocellulosic biomass. While the solubilized components of biomass—cellulose, hemicellulose and lignin—can be separated by the addition of solvents, it is inherently expensive and time consuming additional step. The discovery of enzymes that tolerate high concentrations of IL can make the process more cost effective in two ways—first, the enzymes can be used directly in the solution of IL and biomass to produce sugars from cellulose; and second, if the cellulose is "crashed out", that is, precipitated from the solution using antisolvents like water and ethanol, with a resulting carryover of the IL, then the enzymes can be used to solubilize the cellulosic sugars without need for further washing to remove the IL.

The current method for biomass pretreatment is a two-step process: first step of chemical pretreatment of biomass which is incompatible with the second-step—downstream enzyme hydrolysis. The characteristics of the pretreated biomass like pH and temperature have to be modified so that fungal enzymes, the industrial standard enzymes for hydrolyzing cellulosic sugars, are not compatible with either the temperature or the pH of the solution. This additional step adds time and cost to the overall process. We have shown a method whereby an efficient method of hydrolyzing cellulosic sugars—using extremophilic enzymes—is compatible with an efficient method for pretreating biomass using ionic liquids.

The available commercial enzyme (*T. viridae*, which is commercially available from Sigma-Aldrich; Milwaukee, Wis.) that breaks down cellulose loses more than 50% of its activity in 2.9% EMIM Acetate. As such, it follows that such non-thermostable cellulases have a similar pattern of activity loss. However, as the data shows, 2 thermostable enzymes are found (from *Thermatoga maritima* strain MSB8 (Accession No. NP_229549) and *Pyrococcus horikoshii* strain OT3 (Accession No. NP_143072) which are at least as active in 2.9% EMIM Acetate as in 0% EMIM Acetate. Preliminary results indicate a similar decreasing pattern of activity of *T. viride* enzyme while the enzyme activity of the hyperthermophilic enzymes is unaffected.

A suitable thermostable cellulase is the cellulase of *Thermatoga maritima* strain MSB8 (Accession No. NPX_229549) (or Tma Cel5A), which has the following wild-type amino acid sequence:

```
                                                            (SEQ ID NO: 20)
  1 mgvdpfernk ilgrginign aleapnegdw gvvikdeffd iikeagfshv ripirwstha 61 yafppykimd rffkrvdevi ngalkrglav vinihhyeel mndpeehker flalwkqiad 121 rykdypetlf feilnephgn ltpekwnell eealkvirsi dkkhtiiigt aewggisale 181 klsvpkwekn sivtihyynp fefthqgaew vegsekwlgr kwgspddqkh lieefnfiee 241 wskknkrpiy igefgayrka dlesrikwts fvvremekrr wswaywefcs gfgvydtlrk 301 twnkdlleal iggdsie
```

A suitable thermostable cellulase is the cellulase of *Pyrococcus horikoshii* strain OT3 (Accession No. NP_143072) (or Pho EG), which has the following amino acid sequence:

```
                                                            (SEQ ID NO: 21)
  1 megntilkiv lictilaglf gqvvpvyaen ttyqtptgiy yevrgdtiym invtsgeetp 61 ihlfgvnwfg fetpnhvvhg lwkrnwedml lqikslgfna irlpfctesv kpgtqpigid 121 ysknpdlrgl dslqimekii kkagdlgifv lldyhrigct hieplwyted fseedfintw 181 ievakrfgky wnvigadlkn ephsvtsppa aytdgtgatw gmgnpatdwn laaerigkai 241 lkvaphwlif vegtqftnpk tdssykwgyn awwggnlmav kdypvnlprn klvysphvyg 301 pdvynqpyfg pakgfpdnlp diwyhhfgyv klelgysvvi gefggkyghg gdprdviwqn 361 klvdwmienk fcdffywswn pdsgdtggil qddwttiwed kynnlkrlmd scsksssstq 421 svirsttptk sntskkicgp ailiilavfs lllrrapr
```

In some embodiments of the invention, the composition comprises a cellulose, an ionic liquid and a thermostable cellulase, wherein the thermostable cellulase is capable of hydrolyzing the cellulose.

In some embodiments of the invention, the composition comprises a cellulose, an ionic liquid and a *Thermatoga* or *Pyrococcus* thermostable cellulase, wherein the thermostable cellulase is capable of hydrolyzing the cellulose.

In some embodiments of the invention, the composition comprises a cellulose, an ionic liquid and a *Thermatoga* or *Pyrococcus* thermostable cellulase, wherein the thermostable cellulase is capable of hydrolyzing the cellulose, and IL comprises a 1-alkyl-3-alkylimidazolium alkanate, 1-alkyl-3-alkylimidazolium alkylsulfate, 1-alkyl-3-alkylimidazolium methylsulfonate, 1-alkyl-3-alkylimidazolium hydrogensulfate, 1-alkyl-3-alkylimidazolium thiocyanate, 1-alkyl-3-alkylimidazolium halide, or a mixture thereof, wherein an "alkyl" is an alkyl group comprising from 1 to 10 carbon atoms, and an "alkanate" is an alkanate comprising from 1 to 10 carbon atoms.

Thermostable Cellulase Mutants, and Nucleic Acids Encoding Thereof

The present invention provides for a *Thermatoga maritima* thermostable cellulase mutant with increased cellulase activity. The thermostable cellulase mutant comprises an amino acid sequence having at least 70% identity as compared to the amino acid sequence of wild-type cellulase of *Thermatoga maritima* MSB8 (encoded by the cel5A gene), wherein the amino acid sequence of the thermostable cellulase mutant comprises one or more amino acid residues are altered as compared to the amino acid sequence of the wild-type cellulase. The thermostable cellulase mutant has a cellulase activity higher than that of the wild-type *T. maritima* thermostable cellulase.

In some embodiments of the invention, the thermostable cellulase mutant comprises an amino acid sequence having at least 80% identity as compared to the amino acid sequence of wild-type cellulase. In some embodiments of the invention, the thermostable cellulase mutant comprises an amino acid sequence having at least 90% identity as compared to the amino acid sequence of wild-type cellulase. In some embodiments of the invention, the thermostable cellulase mutant comprises an amino acid sequence having at least 95% identity as compared to the amino acid sequence of wild-type cellulase.

The amino acid sequence of the wild-type thermostable cellulase of *T. maritima* strain MSB8 (Accession No. NP_229549) is depicted by SEQ ID NO:20.

In some embodiments of the invention, the thermostable cellulase mutant has a cellulase activity at least 10% or 15% higher than that of the wild-type *T. maritima* thermostable cellulase when measured under the same conditions. In some embodiments of the invention, the thermostable cellulase mutant has a cellulase activity at least 30% or 40% higher than that of the wild-type *T. maritima* thermostable cellulase when measured under the same conditions. In some embodiments of the invention, the thermostable cellulase mutant has a cellulase activity at least 65% or 75% higher than that of the wild-type *T. maritima* thermostable cellulase when measured under the same conditions. In some embodiments of the invention, the thermostable cellulase mutant has a cellulase activity from 10% to 80% higher than that of the wild-type *T.*

*maritima* thermostable cellulase when measured under the same conditions. In some embodiments of the invention, the thermostable cellulase mutant has a cellulase activity from 30% to 80% higher than that of the wild-type *T. maritima* thermostable cellulase when measured under the same conditions. In some embodiments of the invention, the thermostable cellulase mutant has a cellulase activity from 65% to 80% higher than that of the wild-type *T. maritima* thermostable cellulase when measured under the same conditions.

The present invention provides for a nucleic acid encoding any of the *T. maritima* thermostable cellulase mutants of the present invention. In some embodiments of the invention, the nucleic acid is recombinant or isolated or purified.

In some embodiments of the invention, the thermostable cellulase mutant comprises one or more of the following altered amino acid residues described herein. Examples of the altered amino acid residues include but are not limited to: D29, K35, D40, I92, E98, E106, A113, E132, N140, K155, S177, E202, E209, L231, A256, K304, and E308, wherein each residue is a substituted with an amino acid different from itself. In some embodiments, D29 is substituted with an amino acid comprising a hydrophobic side chain. In some embodiments, K35 is substituted with an amino acid comprising a side chain capable of forming a hydrogen-bond. In some embodiments, D40 is substituted with an amino acid comprising a side chain capable of forming a hydrogen-bond. In some embodiments, I92 is substituted with an amino acid comprising a hydrophobic side chain or a bulky side chain. In some embodiments, E98 is substituted with an amino acid comprising a hydrophobic side chain. In some embodiments, E106 is substituted with an amino acid comprising a hydrophilic side chain. In some embodiments, A113 is substituted with an amino acid comprising a hydrophobic side chain. In some embodiments, E132 is substituted with an amino acid comprising a hydrophilic side chain. In some embodiments, N140 is substituted with an amino acid comprising a side chain capable of forming a hydrogen-bond. In some embodiments, K155 is substituted with an amino acid comprising a hydrophilic side chain. In some embodiments, S177 is substituted with an amino acid comprising a hydrophilic side chain. In some embodiments, E202 is substituted with an amino acid comprising a hydrophilic side chain. In some embodiments, E209 is substituted with an alanine, serine, or cysteine. In some embodiments, L231 is substituted with an amino acid comprising a hydrophilic side chain. In some embodiments, A256 is substituted with an amino acid comprising a side chain capable of forming a hydrogen-bond. In some embodiments, K304 is substituted with an amino acid comprising a hydrophilic side chain. In some embodiments, E308 is substituted with an amino acid comprising a hydrophilic side chain.

An amino acid comprising a hydrophobic side chain includes but is not limited to alanine, valine, isoleucine, leucine, methionine, phenylalanine, and proline. An amino acid comprising a hydrophilic side chain includes but is not limited to histidine, lysine, arginine, aspartic acid, and glutamic acid. An amino acid comprising a side chain capable of forming a hydrogen-bond includes but is not limited to serine, cysteine, threonine, asparagine, glutamine, and tyrosine. An amino acid comprising a bulky side chain includes but is not limited to phenylalanine, tryptophan, tyrosine, and histidine.

In some embodiments of the invention, the thermostable cellulase mutant comprises one or more of the following amino acid substitutions: E98A (Glu→Ala, Glutamic acid to Alanine), E106D (Glu→Asp, Glutamic acid to Aspartic acid), D40N (Asp→Asn, Aspartic acid to Asparagine), L231R (Leu→Arg, Leucine to Arginine), E308K (Glu→Lys, Glutamic acid to Lysine), K155N (Lys→Asn, Lysine to Asparagine), A113V (Ala→Val, Alanine to Valine), E132D (Glu→Asp, Glutamic acid to Aspartic acid), N140S (Asn→Ser, Asparagine to Serine), E202K (Glu→Lys, Glutamic acid to Lysine), K304N (Lys→Asn, Lysine to Asparagine), D29V (Asp→Val, Aspartic acid to Valine), I92F (Ile→Phe, Isoleucine to Phenylalanine), K35N (Lys→Asn, Lysine to Asparagine), E209G (Glu→Gly, Glutamic acid to Glycine), and A256T (Ala→Thr, Alanine to Threonine), and S177R (Ser→Arg, Serine to Arginine). In some embodiments of the invention, the thermostable cellulase mutant comprises two or more of the altered amino acid residues described herein. In some embodiments of the invention, the thermostable cellulase mutant comprises three or more of the altered amino acid residues described herein.

In some embodiments of the invention, the thermostable cellulase mutant comprises one or more groups of the amino acid substitutions as described in Table 6. In some embodiments of the invention, the thermostable cellulase mutant comprises from one to two groups of the amino acid substitutions as described in Table 6. In some embodiments of the invention, the thermostable cellulase mutant comprises from one to three groups of the amino acid substitutions as described in Table 6. In some embodiments of the invention, the thermostable cellulase mutant comprises 4, 5, 6, 7, 8 or 9 groups of the amino acid substitutions as described in Table 6.

TABLE 6

| Group ID | Amino acid substitution(s) |
|---|---|
| Group I | E98A (Glu→Ala, Glutamic acid to Alanine) and E106D (Glu→Asp, Glutamic acid to Aspartic acid) |
| Group II | D40N (Asp→Asn, Aspartic acid to Asparagine) and L231R (Leu→Arg, Leucine to Arginine) |
| Group III | E308K (Glu→Lys, Glutamic acid to Lysine) |
| Group IV | K155N (Lys→Asn, Lysine to Asparagine) |
| Group V | A113V (Ala→Val, Alanine to Valine) |
| Group VI | E132D (Glu→Asp, Glutamic acid to Aspartic acid), N140S (Asn→Ser, Asparagine to Serine), E202K (Glu→Lys, Glutamic acid to Lysine), and K304N (Lys→Asn, Lysine to Asparagine) |
| Group VII | D29V (Asp→Val, Aspartic acid to Valine) and I92F (Ile→Phe, Isoleucine to Phenylalanine) |
| Group VIII | K35N (Lys→Asn, Lysine to Asparagine), E209G (Glu→Gly, Glutamic acid to Glycine), and A256T (Ala→Thr, Alanine to Threonine) |
| Group IX | S177R (Ser→Arg, Serine to Arginine) |

In a particular embodiment of the invention, the thermostable cellulase mutant comprises the amino acid substitutions of Group III and one group chosen from Groups I, II, VI, V, VI, VII, VIII, and IX.

In a particular embodiment of the invention, the thermostable cellulase mutant comprises the amino acid substitutions of Group VI and one group chosen from Groups I, II, III, VI, V, VII, VIII, and IX.

In a particular embodiment of the invention, the thermostable cellulase mutant comprises the amino acid substitutions of Group VIII and one group chosen from Groups I, II, III, VI, V, VI, VII, and IX.

In a particular embodiment of the invention, the thermostable cellulase mutant comprises the amino acid substitutions of Group III, VI, and VIII.

In some embodiments of the invention, the thermostable cellulase mutant comprises the amino acid sequences of any one of the following amino acids sequences depicted in SEQ ID NO: 1-9.

In a particular embodiment of the invention, the thermostable cellulase mutant comprises the amino acid sequences of the wild-type *T. maritima* cellulase except with the following altered amino acid residues: E98A (Glu→Ala, Glutamic acid to Alanine) and E106D (Glu→Asp, Glutamic acid to Aspartic acid).

In a particular embodiment of the invention, the thermostable cellulase mutant comprises the amino acid sequences of:

```
                                          (P1E3; SEQ ID NO: 1)
MGVDPFERNKILGRGINIGNALEAPNEGDWGVVIKDEFFDIIKEAGFSHVRIPIRWSTH

AYAFPPYKIMDRFFKRVDEVINGALKRGLAVVINIHHYAELMNDPEDHKERFLALWK

QIADRYKDYPETLFFEILNEPHGNLTPEKWNELLEEALKVIRSIDKKHTIIIGTAEWGGI

SALEKLSVPKWEKNSIVTIHYYNPFEFTHQGAEWVEGSEKWLGRKWGSPDDQKHLI

EEFNFIEEWSKKNKRPIYIGEFGAYRKADLESRIKWTSFVVREMEKRRWSWAYWEFC

SGFGVYDTLRKTWNKDLLEALIGGDSIE.
```

In a particular embodiment of the invention, the nucleic acid of the invention comprises a nucleotide sequence encoding the amino acid sequence of SEQ ID NO:1.

In a particular embodiment of the invention, the nucleic acid of the invention comprises the following nucleotide sequence:

```
                                          (SEQ ID NO: 10)
ATGGGGGTTGATCCGTTTGAGCGTAATAAAATTCTGGGCCGCGGTATTAA

TATCGGCAACGCACTGGAGGCTCCGAATGAAGGTGATTGGGGCGTGGTTA

TTAAGGATGAATTCTTCGATATTATCAAAGAAGCGGGATTTAGCCATGTG

CGTATTCCGATTCGTTGGTCGACTCATGCCTATGCATTTCCGCCATACAA
```

```
                              -continued
AATTATGGATCGCTTTTTCAAACGTGTGGACGAAGTTATTAACGGTGCCC

TGAAACGCGGACTGGCCGTTGTTATTAATATCCACCACTATGIAGAGCTG

ATGAATGATCCTGAAGMCATAAAGAACGCTTTCTGGCACTGTGGAAACAG

ATTGCGGACCGTTATAAAGATTATCCGGAAACTCTGTTTTTCGAAATTCT

GAACGAGCCGCATGGGAACCTGACGCCGGAAAAATGGAATGAACTGCTGG

AAGAAGCTCTGAAAGTAATCCGTTCGATTGACAAGAAACATACCATCATT

ATTGGCACCGCCGAATGGGGTGGTATCAGTGCACTGGAAAAACTGTCAGT

TCCGAAGTGGGAGAAAAACTCCATTGTGACGATTCATTATTATAACCCGT

TTGAGTTTACCCACCAGGGGGCAGAATGGGTGGAAGGCAGCGAAAAATGG

CTGGGCCGTAAATGGGGTAGTCCTGATGATCAAAAACACCTGATTGAAGA
```

```
                              -continued
GTTTAACTTCATCGAAGAGTGGTCAAAAAAGAATAAACGCCCGATTTATA

TTGGCGAGTTCGGTGCCTATCGCAAAGCTGATCTGGAATCGCGTATTAAA

TGGACAAGTTTTGTTGTACGTGAAATGGAAAAGCGCCGTTGGTCCTGGGC

CTATTGGGAATTCTGTAGCGGTTTTGGTGTCTACGATACGCTGCGCAAAA

CTTGGAACAAAGATCTGCTGGAAGCCCTGATTGGCGGTGACAGTATCGAA

TAA.
```

The cellulase P1E3 has an about 31.77% improvement of its cellulase activity over that of the wild-type *T. maritima* cellulase.

In a particular embodiment of the invention, the thermostable cellulase mutant comprises the amino acid sequences of the wild-type cellulase except with the following altered amino acid residues: D40N (Asp→Asn, Aspartic acid to Asparagine) and L231R (Leu→Arg, Leucine to Arginine).

In a particular embodiment of the invention, the thermostable cellulase mutant comprises the amino acid sequences of:

```
                                          (P2H8; SEQ ID NO: 2)
MGVDPFERNKILGRGINIGNALEAPNEGDWGVVIKDEFFNIIKEAGFSHVRIPIRWSTH

AYAFPPYKIMDRFFKRVDEVINGALKRGLAVVINIHHYEELMNDPEEHKERFLALWK

QIADRYKDYPETLFFEILNEPHGNLTPEKWNELLEEALKVIRSIDKKHTIIIGTAEWGGI

SALEKLSVPKWEKNSIVTIHYYNPFEFTHQGAEWVEGSEKWLGRKWGSPDDQKHRI

EEFNFIEEWSKKNKRPIYIGEFGAYRKADLESRIKWTSFVVREMEKRRWSWAYWEFC

SGFGVYDTLRKTWNKDLLEALIGGDSIE.
```

In a particular embodiment of the invention, the nucleic acid of the invention comprises a nucleotide sequence encoding the amino acid sequence of SEQ ID NO:2.

In a particular embodiment of the invention, the nucleic acid of the invention comprises the following nucleotide sequence:

```
                                          (SEQ ID NO: 11)
ATGGGGGTTGATCCGTTTGAGCGTAATAAAATTCTGGGCCGCGGTATTAA

TATCGGCAACGCACTGGAGGCTCCGAATGAAGGTGATTGGGGCGTGGTTA

TTAAGGATGAATTCTTCAATATTATCAAAGAAGCGGGATTTAGCCATGTG

CGTATTCCGATTCGTTGGTCGACTCATGCCTATGCATTTCCGCCATACAA

AATTATGGATCGCTTTTTCAAACGTGTGGACGAAGTTATTAACGGTGCCC
```

```
TGAAACGCGGACTGGCCGTTGTTATTAATATCCACCACTATGAAGAGCTG

ATGAATGATCCTGAAGAACATAAAGAACGCTTTCTGGCACTGTGGAAACA

GATTGCGGACCGTTATAAAGATTATCCGGAAACTCTGTTTTTCGAAATTC

TGAACGAGCCGCATGGGAACCTGACGCCGGAAAAATGGAATGAACTGCTG

GAAGAAGCTCTGAAAGTAATCCGTTCGATTGACAAGAAACATACCATCAT

TATTGGCACCGCCGAATGGGGTGGTATCAGTGCACTGGAAAAACTGTCAG

TTCCGAAGTGGGAGAAAAACTCCATTGTGACGATTCATTATTATAACCCG

TTTGAGTTTACCCACCAGGGGGCAGAATGGGTGGAAGGCAGCGAAAAATG

GCTGGGCCGTAAATGGGGTAGTCCTGATGATCAAAAACACCGGATTGAAG

AGTTTAACTTCATCGAAGAGTGGTCAAAAAAGAATAAACGCCCGATTTAT

ATTGGCGAGTTCGGTGCCTATCGCAAAGCTGATCTGGAATCGCGTATTAA

ATGGACAAGTTTTGTTGTACGTGAAATGGAAAAGCGCCGTTGGTCCTGGG

CCTATTGGGAATTCTGTAGCGGTTTTGGTGTCTACGATACGCTGCGCAAA

ACTTGGAACAAAGATCTGCTGGAAGCCCTGATTGGCGGTGACAGTATCGA

ATAA.
```

The cellulase P2H8 has an about 40.56% improvement of its cellulase activity over that of the wild-type cellulase.

In a particular embodiment of the invention, the thermostable cellulase comprises the amino acid sequences of the wild-type cellulase except with the following altered amino acid residue: E308K (Glu→Lys, Glutamic acid to Lysine).

In a particular embodiment of the invention, the thermostable cellulase comprises the amino acid sequences of:

```
CGTATTCCGATTCGTTGGTCGACTCATGCCTATGCATTTCCGCCATACAA

AATTATGGATCGCTTTTTCAAACGTGTGGACGAAGTTATTAACGGTGCCC

TGAAACGCGGACTGGCCGTTGTTATTAATATCCACCACTATGAAGAGCTG

ATGAATGATCCTGAAGAACATAAAGAACGCTTTCTGGCACTGTGGAAACA

GATTGCGGACCGTTATAAAGATTATCCGGAAACTCTGTTTTTCGAAATTC

TGAACGAGCCGCATGGGAACCTGACGCCGGAAAAATGGAATGAACTGCTG

GAAGAAGCTCTGAAAGTAATCCGTTCGATTGACAAGAAACATACCATCAT

TATTGGCACCGCCGAATGGGGTGGTATCAGTGCACTGGAAAAACTGTCAG

TTCCGAAGTGGGAGAAAAACTCCATTGTGACGATTCATTATTATAACCCG

TTTGAGTTTACCCACCAGGGGGCAGAATGGGTGGAAGGCAGCGAAAAATG

GCTGGGCCGTAAATGGGGTAGTCCTGATGATCAAAAACACCTGATTGAAG

AGTTTAACTTCATCGAAGAGTGGTCAAAAAAGAATAAACGCCCGATTTAT

ATTGGCGAGTTCGGTGCCTATCGCAAAGCTGATCTGGAATCGCGTATTAA

ATGGACAAGTTTTGTTGTACGTGAAATGGAAAAGCGCCGTTGGTCCTGGG

CCTATTGGGAATTCTGTAGCGGTTTTGGTGTCTACGATACGCTGCGCAAA

ACTTGGAACAAAGATCTGCTGAAAGCCCTGATTGGCGGTGACAGTATCGA

ATAA.
```

The cellulase P3D7 has an about 78.76% improvement of its cellulase activity over that of the wild-type cellulase.

```
                                        (P3D7; SEQ ID NO: 3)
MGVDPFERNKILGRGINIGNALEAPNEGDWGVVIKDEFFDIIKEAGFSHVRIPIRWSTH

AYAFPPYKIMDRFFKRVDEVINGALKRGLAVVINIHHYEELMNDPEEHKERFLALWK

QIADRYKDYPETLFFEILNEPHGNLTPEKWNELLEEALKVIRSIDKKHTIIIGTAEWGGI

SALEKLSVPKWEKNSIVTIHYYNPFEFTHQGAEWVEGSEKWLGRKWGSPDDQKHLI

EEFNFIEEWSKKNKRPIYIGEFGAYRKADLESRIKWTSFVVREMEKRRWSWAYWEFC

SGFGVYDTLRKTWNKDLLKALIGGDSIE.
```

In a particular embodiment of the invention, the nucleic acid of the invention comprises a nucleotide sequence encoding the amino acid sequence of SEQ ID NO:3.

In a particular embodiment of the invention, the nucleic acid of the invention comprises the following nucleotide sequence:

```
                                         (SEQ ID NO: 12)
ATGGGGGTTGATCCGTTTGAGCGTAATAAAATTCTGGGCCGCGGTATTAA

TATCGGCAACGCACTGGAGGCTCCGAATGAAGGTGATTGGGGCGTGGTTA

TTAAGGATGAATTCTTCGATATTATCAAAGAAGCGGGATTTAGCCATGTG
```

In a particular embodiment of the invention, the thermostable cellulase mutant comprises the amino acid sequences of the wild-type T. maritima cellulase except with the following altered amino acid residue: K155N (Lys→Asn, Lysine to Asparagine).

In a particular embodiment of the invention, the thermostable cellulase mutant comprises the amino acid sequences of:

(P4B5; SEQ ID NO: 4)
MGVDPFERNKILGRGINIGNALEAPNEGDWGVVIKDEFFDIIKEAGFSHVRIPIRWSTH

AYAFPPYKIMDRFFKRVDEVINGALKRGLAVVINIHHYEELMNDPEEHKERFLALWK

QIADRYKDYPETLFFEILNEPHGNLTPEKWNELLEEALNVIRSIDKKHTIIIGTAEWGGI

SALEKLSVPKWEKNSIVTIHYYNPFEFTHQGAEWVEGSEKWLGRKWGSPDDQKHLI

EEFNFIEEWSKKNKRPIYIGEFGAYRKADLESRIKWTSFVVREMEKRRWSWAYWEFC

SGFGVYDTLRKTWNKDLLEALIGGDSIE.

In a particular embodiment of the invention, the nucleic acid of the invention comprises a nucleotide sequence encoding the amino acid sequence of SEQ ID NO:4.

In a particular embodiment of the invention, the nucleic acid of the invention comprises the following nucleotide sequence:

(SEQ ID NO: 13)
ATGGGGGTTGATCCGTTTGAGCGTAATAAAATTCTGGGCCGCGGTATTAA

TATCGGCAACGCACTGGAGGCTCCGAATGAAGGTGATTGGGGCGTGGTTA

-continued
TTAAGGATGAATTCTTCGATATTATCAAAGAAGCGGGATTTAGCCATGTG

CGTATTCCGATTCGTTGGTCGACTCATGCCTATGCATTTCCGCCATACAA

AATTATGGATCGCTTTTTCAAACGTGTGGACGAAGTTATTAACGGTGCCC

TGAAACGCGGACTGGCCGTTGTTATTAATATCCACCACTATGAAGAGCTG

ATGAATGATCCTGAAGAACATAAAGAACGCTTTCTGGCACTGTGGAAACA

GATTGCGGACCGTTATAAAGATTATCCGGAAACTCTGTTTTTCGAAATTC

TGAACGAGCCGCATGGGAACCTGACGCCGAAAAATGGAATGAACTGCTG

GAAGAAGCTCTGAATGTAATCCGTTCGATTGACAAGAAACATACCATCAT

TATTGGCACCGCCGAATGGGGTGGTATCAGTGCACTGGAAAAACTGTCAG

TTCCGAAGTGGGAGAAAAACTCCATTGTGACGATTCATTATTATAACCCG

TTTGAGTTTACCCACCAGGGGGCAGAATGGGTGGAAGGCAGCGAAAAATG

GCTGGGCCGTAAATGGGGTAGTCCTGATGATCAAAAACACCTGATTGAAG

AGTTTAACTTCATCGAAGAGTGGTCAAAAAAGAATAAACGCCCGATTTAT

ATTGGCGAGTTCGGTGCCTATCGCAAAGCTGATCTGGAATCGCGTATTAA

ATGGACAAGTTTTGTTGTACGTGAAATGGAAAAGCGCCGTTGGTCCTGGG

CCTATTGGGAATTCTGTAGCGGTTTTGGTGTCTACGATACGCTGCGCAAA

ACTTGGAACAAAGATCTGCTGGAAGCCCTGATTGGCGGTGACAGTATCGA

ATAA.

The cellulase P4B5 has an about 33.02% improvement of its cellulase activity over that of the wild-type cellulase.

In a particular embodiment of the invention, the thermostable cellulase comprises the amino acid sequences of the wild-type T. maritima cellulase except with the following altered amino acid residue: A113V (Ala→Val, Alanine to Valine).

In a particular embodiment of the invention, the thermostable cellulase mutant comprises the amino acid sequences of:

(P8E4; SEQ ID NO: 5)
MGVDPFERNKILGRGINIGNALEAPNEGDWGVVIKDEFFDIIKEAGFSHVRIPIRWSTH

AYAFPPYKIMDRFFKRVDEVINGALKRGLAVVINIHHYEELMNDPEEHKERFLVLWK

QIADRYKDYPETLFFEILNEPHGNLTPEKWNELLEEALKVIRSIDKKHTIIIGTAEWGGI

SALEKLSVPKWEKNSIVTIHYYNPFEFTHQGAEWVEGSEKWLGRKWGSPDDQKHLI

EEFNFIEEWSKKNKRPIYIGEFGAYRKADLESRIKWTSFVVREMEKRRWSWAYWEFC

SGFGVYDTLRKTWNKDLLEALIGGDSIE.

In a particular embodiment of the invention, the nucleic acid of the invention comprises a nucleotide sequence encoding the amino acid sequence of SEQ ID NO:5.

In a particular embodiment of the invention, the nucleic acid of the invention comprises the following nucleotide sequence:

(SEQ ID NO: 14)
ATGGGGGTTGATCCGTTTGAGCGTAATAAAATTCTGGGCCGCGGTATTAA

TATCGGCAACGCACTGGAGGCTCCGAATGAAGGTGATTGGGGCGTGGTTA

TTAAGGATGAATTCTTCGATATTATCAAAGAAGCGGGATTTAGCCATGTG

CGTATTCCGATTCGTTGGTCGACTCATGCCTATGCATTTCCGCCATACAA

AATTATGGATCGCTTTTTCAAACGTGTGGACGAAGTTATTAACGGTGCCC

TGAAACGCGGACTGGCCGTTGTTATTAATATCCACCACTATGAAGAGCTG

ATGAATGATCCTGAAGAACATAAAGAACGCTTTCTGGTACTGTGGAAACA

GATTGCGGACCGTTATAAAGATTATCCGGAAACTCTGTTTTTCGAAATTC

TGAACGAGCCGCATGGGAACCTGACGCCGGAAAAATGGAATGAACTGCTG

GAAGAAGCTCTGAAAGTAATCCGTTCGATTGACAAGAAACATACCATCAT

TATTGGCACCGCCGAATGGGGTGGTATCAGTGCACTGGAAAAACTGTCAG

TTCCGAAGTGGGAGAAAAACTCCATTGTGACGATTCATTATTATAACCCG

TTTGAGTTTACCCACCAGGGGGCAGAATGGGTGGAAGGCAGCGAAAAATG

GCTGGGCCGTAAATGGGGTAGTCCTGATGATCAAAAACACCTGATTGAAG

```
AGTTTAACTTCATCGAAGAGTGGTCAAAAAAGAATAAACGCCCGATTTAT

ATTGGCGAGTTCGGTGCCTATCGCAAAGCTGATCTGGAATCGCGTATTAA

ATGGACAAGTTTTGTTGTACGTGAAATGGAAAAGCGCCGTTGGTCCTGGG

CCTATTGGGAATTCTGTAGCGGTTTTGGTGTCTACGATACGCTGCGCAAA

ACTTGGAACAAAGATCTGCTGGAAGCCCTGATTGGCGGTGACAGTATCGA

ATAA.
```

The cellulase P8E4 has an about 49.06% improvement of its cellulase activity over that of the wild-type *T. maritima* cellulase.

In a particular embodiment of the invention, the thermostable cellulase mutant comprises the amino acid sequences of the wild-type *T. maritima* cellulase except with the following altered amino acid residue: E132D (Glu→Asp, Glutamic acid to Aspartic acid), N140S (Asn→Ser, Asparagine to Serine), E202K (Glu→Lys, Glutamic acid to Lysine), and K304N (Lys→Asn, Lysine to Asparagine).

In a particular embodiment of the invention, the thermostable cellulase mutant comprises the amino acid sequences of:

```
                                       (P13F6; SEQ ID NO: 6)
MGVDPFERNKILGRGINIGNALEAPNEGDWGVVIKDEFFDIIKEAGFSHVRIPIRWSTH

AYAFPPYKIMDRFFKRVDEVINGALKRGLAVVINIHHYEELMNDPEEHKERFLALWK

QIADRYKDYPETLFFDILNEPHGSLTPEKWNELLEEALKVIRSIDKKHTIIIGTAEWGGI

SALEKLSVPKWEKNSIVTIHYYNPFKFTHQGAEWVEGSEKWLGRKWGSPDDQKHLI

EEFNFIEEWSKKNKRPIYIGEFGAYRKADLESRIKWTSFVVREMEKRRWSWAYWEFC

SGFGVYDTLRKTWNNDLLEALIGGDSIE.
```

In a particular embodiment of the invention, the nucleic acid of the invention comprises a nucleotide sequence encoding the amino acid sequence of SEQ ID NO:6.

In a particular embodiment of the invention, the nucleic acid of the invention comprises the following nucleotide sequence:

```
                                              (SEQ ID NO: 15)
ATGGGGGTTGATCCGTTTGAGCGTAATAAAATTCTGGGCCGCGGTATTAA

TATCGGCAACGCACTGGAGGCTCCGAATGAAGGTGATTGGGGCGTGGTTA

TTAAGGATGAATTCTTCGATATTATCAAAGAAGCGGGATTTAGCCATGTG

CGTATTCCGATTCGTTGGTCGACTCATGCCTATGCATTTCCGCCATACAA

AATTATGGATCGCTTTTTCAAACGTGTGGACGAAGTTATTAACGGTGCCC

TGAAACGCGGACTGGCCGTTGTTATTAATATCCACCACTATGAAGAGCTG

ATGAATGATCCTGAAGAACATAAAGAACGCTTTCTGGCACTGTGGAAACA

GATTGCGGACCGTTATAAAGATTATCCGGAAACTCTGTTTTTCGATATTC

TGAACGAGCCGCATGGGAGCCTGACGCCGGAAAAATGGAATGAACTGCTG

GAAGAAGCTCTGAAAGTAATCCGTTCGATTGACAAGAAACATACCATCAT

TATTGGCACCGCCGAATGGGTGGTATCAGTGCACTGGAAAAACTGTCAG

TTCCGAAGTGGGAGAAAAACTCCATTGTGACGATTCATTATTATAACCCG

TTTAAGTTTACACACCAGGGGGCAGAATGGGTGGAAGGCAGCGAAAAATG
```

```
GCTGGGCCGTAAATGGGGTAGTCCTGACGATCAAAAACACCTGATTGAAG

AGTTTAACTTCATCGAAGAGTGGTCAAAAAAGAATAAACGCCCGATTTAT

ATTGGCGAGTTCGGTGCCTATCGCAAAGCTGATCTGGAATCGCGGATTAA

ATGGACAAGTTTTGTTGTACGTGAAATGGAAAAGCGCCGTTGGTCCTGGG

CCTATTGGGAATTCTGTAGCGGTTTTGGTGTCTACGATACGCTGCGCAAA

ACTTGGAACAACGATCTGCTGGAAGCCCTGATTGGCGGTGACAGTATCGA

ATAA.
```

The cellulase P13F6 has an about 68.51% improvement of its cellulase activity over that of the wild-type *T. maritima* cellulase.

In a particular embodiment of the invention, the thermostable cellulase mutant comprises the amino acid sequences of the wild-type *T. maritima* cellulase except with the following altered amino acid residue: D29V (Asp→Val, Aspartic acid to Valine) and I92F (Ile→Phe, Isoleucine to Phenylalanine).

In a particular embodiment of the invention, the thermostable cellulase mutant comprises the amino acid sequences of:

```
                                     (P15B10; SEQ ID NO: 7)
MGVDPFERNKILGRGINIGNALEAPNEGVWGVVIKDEFFDIIKEAGFSHV

RIPIRWSTHAYAFPPYKIMDRFFKRVDEVINGALKRGLAVVFNIHHYEEL

MNDPEEHKERFLALWKQIADRYKDYPETLFFEILNEPHGNLTPEKWNELL

EEALKVIRSIDKKHTIIIGTAEWGGISALEKLSVPKWEKNSIVTIHYYNP

FEFTHQGAEWVEGSEKWLGRKWGSPDDQKHLIEEFNFIEEWSKKNKRPIY

IGEFGAYRKADLESRIKWTSFVVREMEKRRWSWAYWEFCSGFGVYDTLRK

TWNKDLLEALIGGDSIE.
```

In a particular embodiment of the invention, the nucleic acid of the invention comprises a nucleotide sequence encoding the amino acid sequence of SEQ ID NO:7.

In a particular embodiment of the invention, the nucleic acid of the invention comprises the following nucleotide sequence:

```
                                              (SEQ ID NO: 16)
ATGGGGGTTGATCCGTTTGAGCGTAATAAAATTCTGGGCCGCGGTA

TTAATATCGGCAACGCACTGGAGGCTCCGAATGAAGGTGITTGGGGTGTG

GTTATTAAGGATGAATTCTTCGATATTATCAAAGAAGCGGGATTTAGCCA

TGTGCGTATTCCGATTCGTTGGTCGACTCATGCCTATGCATTTCCGCCAT

ACAAAATTATGGATCGCTTTTTCAAACGTGTGGACGAAGTTATTAACGGT
```

-continued

```
GCCCTGAAACGCGGACTGGCCGTTGTTTTTAATATCCACCACTATGAAGA

GCTGATGAATGATCCTGAAGAACATAAAGAACGCTTTCTGGCACTGTGGA

AACAGATTGCGGACCGTTATAAAGATTATCCGGAAACTCTGTTTTTCGAA

ATTCTGAACGAGCCGCATGGGAACCTGACGCCGGAAAAATGGAATGAACT

GCTGGAAGAAGCTCTGAAAGTAATCCGTTCGATTGACAAGAAACATACCA

TCATTATTGGCACCGCCGAATGGGGTGGTATCAGTGCACTGGAAAAACTG

TCAGTTCCGAAGTGGGAGAAAAACTCCATTGTGACGATTCATTATTATAA

CCCGTTTGAGTTTACCCACCAGGGGGCAGAATGGGTGGAAGGCAGCGAAA

AATGGCTGGGCCGTAAATGGGGTAGTCCTGATGATCAAAAACACCTGATT

GAAGAGTTTAACTTCATCGAAGAGTGGTCAAAAAAGAATAAACGCCCGAT

TTATATTGGCGAGTTCGGTGCCTATCGCAAAGCTGATCTGGAATCGCGTA

TTAAATGGACAAGTTTTGTTGTACGTGAAATGGAAAAGCGCCGTTGGTCC

TGGGCCTATTGGGAATTCTGTAGCGGTTTTGGTGTCTACGATACGCTGCG

CAAAACTTGGAACAAAGATCTGCTGGAAGCCCTGATTGGCGGTGACAGTA

TCGAATAA.
```

The cellulase P15B10 has an about 33.79% improvement of its cellulase activity over that of the wild-type T. maritima cellulase.

In a particular embodiment of the invention, the thermostable cellulase mutant comprises the amino acid sequences of the wild-type T. maritima cellulase except with the following altered amino acid residue: K35N (Lys→Asn, Lysine to Asparagine), E209G (Glu→Gly, Glutamic acid to Glycine), and A256T (Ala→Thr, Alanine to Threonine).

In a particular embodiment of the invention, the thermostable cellulase mutant comprises the amino acid sequences of:

```
                              (P15G2; SEQ ID NO: 8)
MGVDPFERNKILGRGINIGNALEAPNEGDWGVVINDEFFDIIKEAGFSHVRIPIRWSTH

AYAFPPYKIMDRFFKRVDEVINGALKRGLAVVINIHHYEELMNDPEEHKERFLALWK

QIADRYKDYPETLFFEILNEPHGNLTPEKWNELLEEALKVIRSIDKKHTIIIGTAEWGGI

SALEKLSVPKWEKNSIVTIHYYNPFEFTHQGAGWVEGSEKWLGRKWGSPDDQKHLI

EEFNFIEEWSKKNKRPIYIGEFGTYRKADLESRIKWTSFVVREMEKRRWSWAYWEFC

SGFGVYDTLRKTWNKDLLEALIGGDSIE.
```

In a particular embodiment of the invention, the nucleic acid of the invention comprises a nucleotide sequence encoding the amino acid sequence of SEQ ID NO:8.

In a particular embodiment of the invention, the nucleic acid of the invention comprises the following nucleotide sequence:

```
                              (SEQ ID NO: 17)
ATGGGGGTTGATCCGTTTGAGCGTAATAAAATTCTGGGCCGCGGTATTAA

TATCGGCAACGCACTGGAGGCTCCGAATGAAGGTGATTGGGGTGTGGTTA

TTAATGATGAATTCTTCGATATTATCAAAGAAGCGGGATTTAGCCATGTG

CGTATTCCGATTCGTTGGTCGACTCATGCCTATGCATTTCCGCCATACAA

AATTATGGATCGCTTTTTCAAACGTGTGGACGAAGTTATTAACGGTGCCC

TGAAACGCGGACTGGCCGTTGTTATTAATATCCACCACTATGAAGAGCTG

ATGAATGATCCTGAAGAACATAAAGAACGCTTTCTGGCACTGTGGAAACA

GATTGCGGACCGTTATAAAGATTATCCGGAAACTCTGTTTTTCGAAATTC

TGAACGAGCCGCATGGGAACCTGACGCCGGAAAAATGGAATGAACTGCTG

GAAGAAGCTCTGAAAGTAATCCGTTCGATTGACAAGAAACATACCATCAT

TATTGGCACCGCCGAATGGGGTGGTATCAGTGCACTGGAAAAACTGTCAG

TTCCGAAGTGGGAGAAAAACTCCATTGTGACGATTCATTATTATAACCCG

TTTGAGTTTACCCACCAGGGGGCAGGATGGGTGGAAGGCAGCGAAAAATG

GCTGGGCCGTAAATGGGGTAGTCCTGATGATCAAAAACACCTGATTGAAG

AGTTTAACTTCATCGAAGAGTGGTCAAAAAAGAATAAACGCCCGATTTAT

ATTGGCGAGTTCGGTACCTATCGCAAAGCTGATCTGGAATCGCGTATTAA

ATGGACAAGTTTTGTTGTACGTGAAATGGAAAAGCGCCGTTGGTCCTGGG

CCTATTGGGAATTCTGTAGCGGTTTTGGTGTCTACGATACGCTGCGCAAA

ACTTGGAACAAAGATCTGCTGGAAGCCCTGATTGGCGGTGACAGTATCGA

ATAA.
```

The cellulase P15G2 has an about 66.92% improvement of its cellulase activity over that of the wild-type T. maritima cellulase.

In a particular embodiment of the invention, the thermostable cellulase mutant comprises the amino acid sequences of the wild-type T. maritima cellulase except with the following altered amino acid residue: S177R (Ser→Arg, Serine to Arginine).

In a particular embodiment of the invention, the thermostable cellulase mutant comprises the amino acid sequences of:

(P15H11; SEQ ID NO: 22)
MGVDPFERNKILGRGINIGNALEAPNEGDWGVVIKDEFFDIIKEAGFSHVRIPIRWSTH

AYAFPPYKIMDRFFKRVDEVINGALKRGLAVVINIHHYEELMNDPEEHKERFLALWK

QIADRYKDYPETLFFEILNEPHGNLTPEKWNELLEEALKVIRSIDKKHTIIIGTAEWGGI

RALEKLSVPKWEKNSIVTIHYYNPFEFTHQGAEWVEGSEKWLGRKWGSPDDQKHLI

EEFNFIEEWSKKNKRPIYIGEFGAYRKADLESRIKWTSFVVREMEKRRWSWAYWEFC

SGFGVYDTLRKTWNKDLLEALIGGDSIE.

In a particular embodiment of the invention, the nucleic acid of the invention comprises a nucleotide sequence encoding the amino acid sequence of SEQ ID NO:22.

In a particular embodiment of the invention, the nucleic acid of the invention comprises the following nucleotide sequence:

(SEQ ID NO: 18)
ATGGGGGTTGATCCGTTTGAGCGTAATAAAATTCTGGGCCGCGGTATTAA

TATCGGCAACGCACTGGAGGCTCCGAATGAAGGTGATTGGGCGTGGTTA

TTAAGGATGAATTCTTCGATATTATCAAAGAAGCGGGATTTAGCCATGTG

CGTATTCCGATTCGTTGGTCGACTCATGCCTATGCATTTCCGCCATACAA

AATTATGGATCGCTTTTTCAAACGTGTGGACGAAGTTATTAACGGTGCCC

TGAAACGCGGACTGGCCGTTGTTATTAATATCCACCACTATGAAGAGCTG

ATGAATGATCCTGAAGAACATAAAGAACGCTTTCTGGCACTGTGGAAACA

GATTGCGGACCGTTATAAAGATTATCCGGAAACTCTGTTTTTCGAAATTC

TGAACGAGCCGCATGGGAACCTGACGCCGGAAAAATGGAATGAACTGCTG

GAAGAAGCTCTGAAAGTAATCCGTTCGATTGACAAGAAACATACCATCAT

TATTGGCACCGCCGAATGGGGTGGTATCAGAGCACTGGAAAAACTGTCAG

TTCCGAAGTGGGAGAAAAACTCCATTGTGACGATTCATTATTATAACCCG

TTTGAGTTTACCCACCAGGGGGCAGAATGGGTGGAAGGCAGCGAAAAATG

GCTGGGCCGTAAATGGGGTAGTCCTGATGATCAAAAACACCTGATTGAAG

AGTTTAACTTCATCGAAGAGTGGTCAAAAAAGAATAAACGCCCGATTTAT

ATTGGCGAGTTCGGTGCCTATCGCAAAGCTGATCTGGAATCGCGTATTAA

ATGGACAAGTTTTGTTGTACGTGAAATGGAAAAGCGCCGTTGGTCCTGGG

CCTATTGGGAATTCTGTAGCGGTTTTGGTGTCTACGATACGCTGCGCAAA

ACTTGGAACAAAGATCTGCTGGAAGCCCTGATTGGCGGTGACAGTATCGA

ATAA.

The cellulase P15H11 has an about 35.98% improvement of its cellulase activity over that of the wild-type T. maritima cellulase.

The thermostable cellulase mutant has an enzymatic activity for hydrolyzing cellulose, hemicelluloses, or lignocelluloses that has an optimal temperature that is equal to or more than 65° C. In some embodiments, optimal temperature is equal to or more than 85° C. In some embodiments, optimal temperature is equal to or more than 90° C. In some embodiments, optimal temperature is equal to or more than 95° C.

Host Cells for Producing the Thermostable Cellulase Mutant

The present invention provides for a host cell comprising a nucleic acid of the present invention.

The nucleic acid constructs of the present invention comprise nucleic acid sequences encoding one or more of the subject thermostable cellulase mutants. The nucleic acid of the subject thermostable cellulase mutants are operably linked to promoters and optionally control sequences such that the subject enzymes are expressed in a host cell cultured under suitable conditions. The promoters and control sequences are specific for each host cell species. In some embodiments, expression vectors comprise the nucleic acid constructs. Methods for designing and making nucleic acid constructs and expression vectors are well known to those skilled in the art.

Sequences of nucleic acids encoding the subject thermostable cellulase mutant can be prepared by any suitable method known to those of ordinary skill in the art, including, for example, direct chemical synthesis or cloning.

Each nucleic acid sequence encoding the desired subject thermostable cellulase mutant can be incorporated into an expression vector. Incorporation of the individual nucleic acid sequences may be accomplished through known methods that include, for example, the use of restriction enzymes (such as BamHI, EcoRI, HhaI, XhoI, XmaI, and so forth) to cleave specific sites in the expression vector, e.g., plasmid. The restriction enzyme produces single stranded ends that may be annealed to a nucleic acid sequence having, or synthesized to have, a terminus with a sequence complementary to the ends of the cleaved expression vector. Annealing is performed using an appropriate enzyme, e.g., DNA ligase. As will be appreciated by those of ordinary skill in the art, both the expression vector and the desired nucleic acid sequence are often cleaved with the same restriction enzyme, thereby assuring that the ends of the expression vector and the ends of the nucleic acid sequence are complementary to each other. In addition, DNA linkers may be used to facilitate linking of nucleic acids sequences into an expression vector.

A series of individual nucleic acid sequences can also be combined by utilizing methods that are known to those having ordinary skill in the art (e.g., U.S. Pat. No. 4,683,195).

For example, each of the desired nucleic acid sequences can be initially generated in a separate PCR. Thereafter, specific primers are designed such that the ends of the PCR products contain complementary sequences. When the PCR products are mixed, denatured, and reannealed, the strands having the matching sequences at their 3' ends overlap and can act as primers for each other Extension of this overlap by DNA polymerase produces a molecule in which the original sequences are "spliced" together. In this way, a series of individual nucleic acid sequences may be "spliced" together and subsequently transduced into a host microorganism simultaneously. Thus, expression of each of the plurality of nucleic acid sequences is effected.

Individual nucleic acid sequences, or "spliced" nucleic acid sequences, are then incorporated into an expression vector. The invention is not limited with respect to the process by which the nucleic acid sequence is incorporated into the expression vector. Those of ordinary skill in the art are familiar with the necessary steps for incorporating a nucleic acid sequence into an expression vector. A typical expression vector contains the desired nucleic acid sequence preceded by one or more regulatory regions, along with a ribosome binding site, e.g., a nucleotide sequence that is 3-9 nucleotides in length and located 3-11 nucleotides upstream of the initiation codon in *E. coli*. See Shine et al. (1975) *Nature* 254:34 and Steitz, in Biological Regulation and Development: Gene Expression (ed. R. F. Goldberger), vol. 1, p. 349, 1979, Plenum Publishing, N.Y.

Regulatory regions include, for example, those regions that contain a promoter and an operator. A promoter is operably linked to the desired nucleic acid sequence, thereby initiating transcription of the nucleic acid sequence via an RNA polymerase enzyme. An operator is a sequence of nucleic acids adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. Examples include lactose promoters (LacI repressor protein changes conformation when contacted with lactose, thereby preventing the Lad repressor protein from binding to the operator) and tryptophan promoters (when complexed with tryptophan, TrpR repressor protein has a conformation that binds the operator; in the absence of tryptophan, the TrpR repressor protein has a conformation that does not bind to the operator). Another example is the tac promoter. (See deBoer et al. (1983) *Proc. Natl. Acad. Sci. USA*, 80:21-25.) As will be appreciated by those of ordinary skill in the art, these and other expression vectors may be used in the present invention, and the invention is not limited in this respect.

Although any suitable expression vector may be used to incorporate the desired sequences, readily available expression vectors include, without limitation: plasmids, such as pSC101, pBR322, pBBR1MCS-3, pUR, pEX, pMR100, pCR4, pBAD24, pUC19; bacteriophages, such as M13 phage and λ phage. Of course, such expression vectors may only be suitable for particular host cells. One of ordinary skill in the art, however, can readily determine through routine experimentation whether any particular expression vector is suited for any given host cell. For example, the expression vector can be introduced into the host cell, which is then monitored for viability and expression of the sequences contained in the vector. In addition, reference may be made to the relevant texts and literature, which describe expression vectors and their suitability to any particular host cell.

The expression vectors of the invention must be introduced or transferred into the host cell. Such methods for transferring the expression vectors into host cells are well known to those of ordinary skill in the art. For example, one method for transforming *E. coli* with an expression vector involves a calcium chloride treatment wherein the expression vector is introduced via a calcium precipitate. Other salts, e.g., calcium phosphate, may also be used following a similar procedure. In addition, electroporation (i.e., the application of current to increase the permeability of cells to nucleic acid sequences) may be used to transfect the host microorganism. Also, microinjection of the nucleic acid sequencers) provides the ability to transfect host microorganisms. Other means, such as lipid complexes, liposomes, and dendrimers, may also be employed. Those of ordinary skill in the art can transfect a host cell with a desired sequence using these or other methods.

For identifying a transfected host cell, a variety of methods are available. For example, a culture of potentially transfected host cells may be separated, using a suitable dilution, into individual cells and thereafter individually grown and tested for expression of the desired nucleic acid sequence. In addition, when plasmids are used, an often-used practice involves the selection of cells based upon antimicrobial resistance that has been conferred by genes intentionally contained within the expression vector, such as the amp, gpt, neo, and hyg genes.

The host cell is transformed with at least one expression vector. When only a single expression vector is used (without the addition of an intermediate), the vector will contain all of the nucleic acid sequences necessary.

Once the host cell has been transformed with the expression vector, the host cell is allowed to grow. This process entails culturing the host cells in a suitable medium. As the host cell grows and/or multiplies, expression of the thermostable cellulase mutant is effected. Any means for recovering the thermostable cellulase mutant from the host cell may be used. The thermostable cellulase mutant can be isolated or purified using methods well known to those skilled in the art.

The present invention provides for a method for producing a thermostable cellulase mutant of the present invention comprising: providing a host cell capable of expressing the thermostable cellulase mutant, culturing the host cell in a culture medium under conditions whereby the thermostable cellulase mutant is produced, optionally isolating the thermostable cellulase mutant from the host cell and/or the culture medium, and optionally contacting the thermostable cellulase mutant and a cellulose, whereby the cellulose is hydrolyzed by the thermostable cellulase mutant.

In some embodiments of the invention, the providing step comprises: introducing an expression vector capable of expressing the thermostable cellulase mutant in the host cell into the host cell, and optionally constructing the expression vector encoding a promoter operatively linked to a nucleic acid encoding the thermostable cellulase mutant, wherein the constructing step precedes the introducing step.

Applications

The present invention provides for a composition comprising the *T. maritima* thermostable cellulase mutant of the present invention. In some embodiments, the thermostable cellulase mutant is isolated or purified.

In some embodiments of the invention, the composition further comprises an ionic liquid. In some embodiments of the invention, the composition further comprises a cellulose, wherein the thermostable cellulase mutant is capable of hydrolyzing the cellulose. In some embodiments of the invention, the composition further comprises an ionic liquid and a cellulose, wherein the thermostable cellulase is capable of hydrolyzing the cellulose. In some embodiments of the invention, the composition comprises a pretreatment biomass.

The present invention provides for a method of hydrolyzing a cellulose, comprising: providing a composition comprising a solution comprising an ionic liquid, a cellulose, and a thermostable cellulase mutant of the present invention to the solution, such that the cellulose is hydrolyzed by the thermostable cellulase mutant. In some embodiments of the invention, the solution comprises a pretreatment biomass.

The present invention provides for a method for converting of the carbohydrates of lignocellulose to sugars with improvements in yield and rate of sugar production has been developed by using thermostable cellulase mutant of the invention. In some embodiments of the invention, the thermostable cellulase mutant is compatible with ionic liquid (IL). In some embodiments, the pretreatment biomass is a pretreatment cellulose biomass, pretreatment hemicellulose biomass, pretreatment lingo-cellulose biomass, or a mixture thereof. The present invention provides for a method for converting lignocellulosic biomass to sugars for the production of biofuels using the thermostable cellulase mutant. Methods for the pretreatment of biomass and the downstream enzymatic hydrolysis that is required to breakdown the long polymers of cellulose to simpler sugars for biofuels production.

The thermostable cellulase mutants of the invention can be used in the hydrolysis of pretreated biomass for the production of sugars from biomass. The sugars can be used in all process that use C6 sugars, such as glucose, as the enzymes and the process has shown to hydrolyze cellulose sugars and the resulting sugars can be used for any intended purpose. The process is of significant interest in biomass processing or biofuels and other biomaterials, paper recycling and pulp processing for paper manufacturing.

The present invention can be used in the hydrolysis of pretreated biomass for the production of sugars from biomass. The sugars can be used in all process that use C6 sugars, such as glucose, as the enzymes and the process has shown to hydrolyze cellulose sugars and the resulting sugars can be used for any intended purpose. The process is of significant interest in biomass processing or biofuels and other biomaterials, paper recycling and pulp processing for paper manufacturing.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

EXAMPLE 1

Thermostable Cellulases have Unchanged Enzymatic Activity in Up to 2.9% IL

Enzymatic hydrolysis is the rate limiting step in the fermentation of biomass to sugars. The main barrier is the highly crystalline structure of cellulose that limits accessibility to enzyme adsorption sites and slows the hydrolysis of cellulose to sugars in aqueous media. To increase enzyme accessibility, a combination of high temperature and extremes of pH are used during common pretreatment steps like dilute acid or ammonia fiber explosion. IL are a new class of environment friendly, non-volatile solvents used in the pretreatment of cellulosic biomass. IL's have been shown to dissolve cellulose which can be recovered in the amorphous form by the addition of antisolvents like water. However, significant decreases in cellulase activity in the presence of trace amounts of IL's have been reported in literature, necessitating extensive processing to remove residual IL's from the regenerated cellulose. To simplify the entire process, it is necessary to develop cellulases that are stable and active in the presence of trace amounts of IL's. Extremophilic enzymes are suitable for use with the IL, such as 1-ethyl-3-methylimidazolium acetate (EMIM Acetate). The endoglucanase from the hyperthermophilic bacterium *Thermatoga maritima* (Tma cellulase) is purified by affinity chromatography and the enzymatic hydrolysis activity is measured in the presence of varying concentrations of EMIM Acetate. A comparison of the enzymatic efficiency between the commercially available *T. viride* cellulase from Sigma and the Tma cellulase and the differences related to biochemical properties. Tma cellulose was found to be more stable in the presence of trace amounts of EMIM acetate.

Figure 2:
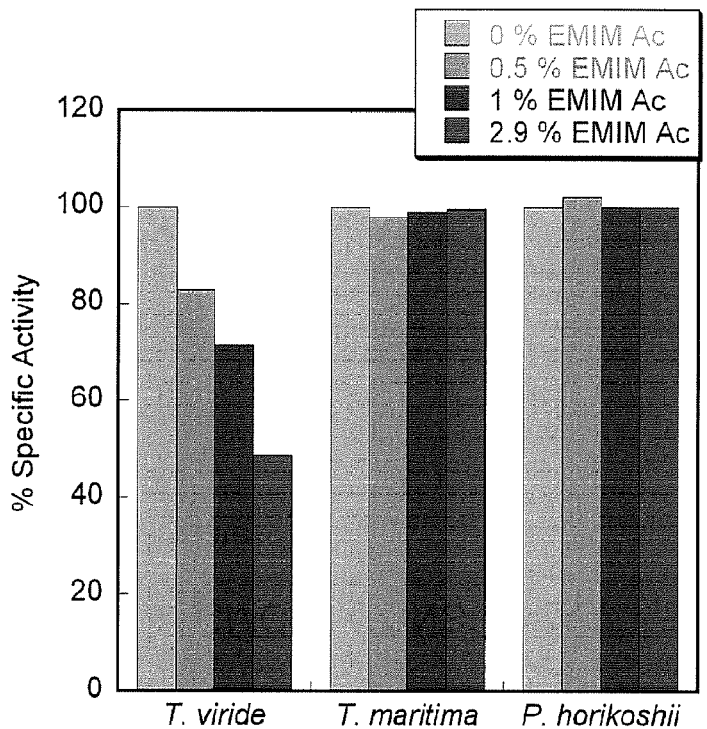
FIG. 2 shows the % specific activities of the cellulase enzyme of *T. viride*, and the endoglucanase of *T. maritima* and *P. horikoshii*.
Figure 3:
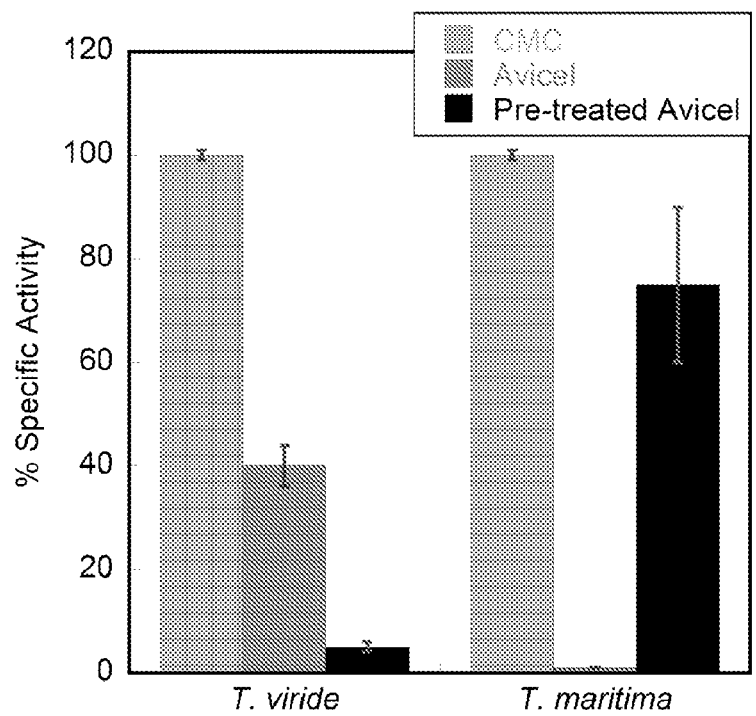
FIG. 3 shows that the *T. maritima* endoglucanase is more tolerant to EMIM Acetate as compared to that of *T. viride*.
Figure 4:
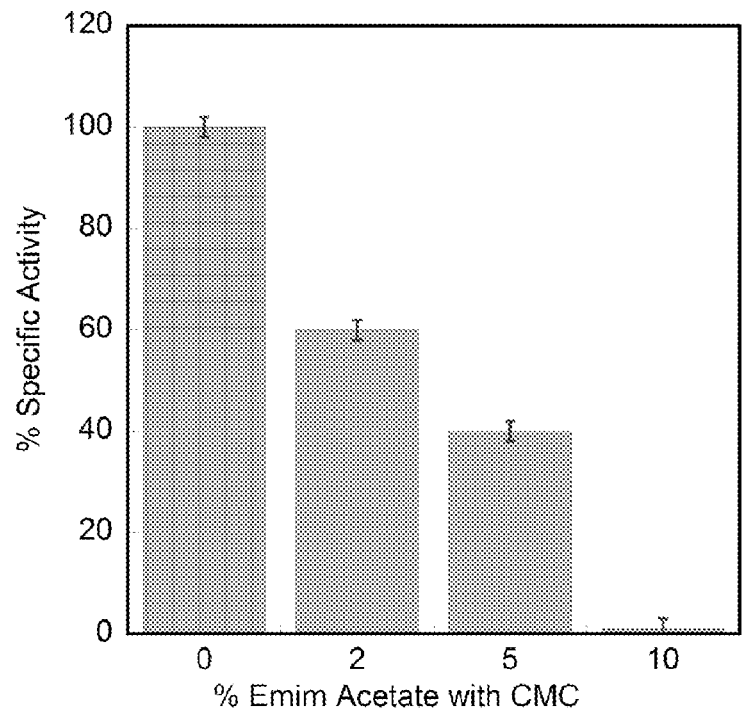
FIG. 4 shows the % specific activity of *T. viride* cellulase over an increasing concentration of EMIM Acetate.
Figure 5:
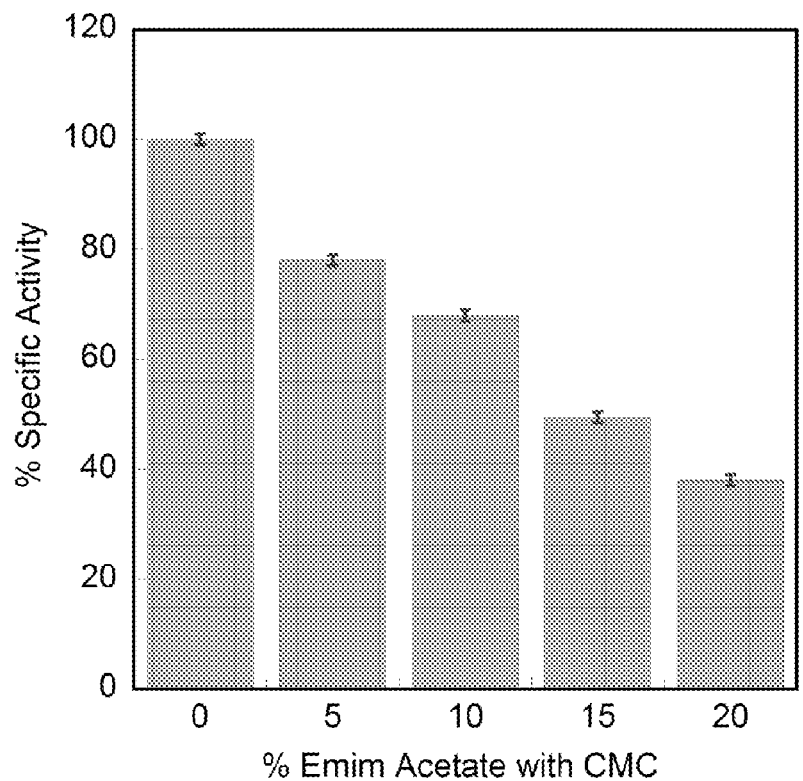
FIG. 5 shows the % specific activity of *T. maritima* endoglucanase over an increasing concentration of EMIM Acetate.

The enzymetic activity of the cellulases of *Trichoderma viride, Thermatoga maritima*, and *Pyrococcus horikoshii* are measured under varying concentrations of EMIM Acetate. FIG. 2 shows that the activity of the industrial standard enzyme from *T. viride* shows a rapid decline (~50% decline in specific activity as the concentration of EMIM Acetate is varied from 0% to 2.9% (by volume)). The endoglucanase enzymes from the hyperthermophilic bacterium *T. maritima* and the hyperthermophilic archaeon *P. horikoshii* remain unchanged under the same conditions. The enzymes activities are calculated using both the Azo-CMC assay and the DNS assay. FIG. 3 shows that *T. maritima* endoglucanase is more tolerant to EMIM Acetate as compared to *T. viride* endoglucanase. FIGS. 4 and 5 show that *T. maritima* endoglucanase has a higher IL tolerance as compared to *T. viride* endoglucanase. At 10% EMIM Acetate the % specific activity of *T. viride* endoglucanase is near 0%, while at 20% EMIM Acetate the % specific activity of *T. maritima* endoglucanase is nearly 40%.

EXAMPLE 2

Cellulase Enzymatic Activity Assay on Soluble Substrates

Enzymatic activity is measured on soluble polysaccharide substrates, CMC, using the dinitrosalicylic acid reducing sugar assay. Briefly, CMC (2% w/v) in 120 µA acetate buffer, (100 mM, pH 4.8) is incubated with enzyme at 80° C. for 30 minutes for Tma and 37° C. and 10 minutes for *T. viride*. The solution is cooled down to 4° C. and 80 µL of DNS solution is added. The reactants are incubated at 95° C. for 5 minutes and cooled down to room temperature before the absorbance is read at 540 nm. The reducing sugar concentration in the sample is calculated from its absorbance using the standard curve of D-glucose. All experiments are run in triplicate.

EXAMPLE 3

*T. martima* Endoglucanase is More Tolerant to IL Compared to *T. viride* Cellulase The recombinant endoglucanase from the extremophile *T. maritima* is more tolerant to ionic liquids compared to the commercially available *T. viride* cellulase (Sigma). Increasing concentrations of IL destabilize protein secondary structures and lead to decreased catalytic efficiencies.

TABLE 2

*T. viride* $T_m$ decreases with higher EMIM Acetate concentration.

| % EMIM Acetate | Melting Temp. (° C.) | $\Delta T_m$ |
|---|---|---|
| 0 | 65.2 | — |
| 2 | 58.9 | 6.3 |

TABLE 2-continued

T. viride $T_m$ decreases with higher EMIM Acetate concentration.

| % EMIM Acetate | Melting Temp. (° C.) | Δ $T_m$ |
|---|---|---|
| 5 | 55.4 | 9.8 |
| 10 | 49.5 | 15.7 |

TABLE 3

T. maritima $T_m$ decreases with higher EMIM Acetate concentration.

| % EMIM Acetate | Melting Temp. (° C.) | Δ $T_m$ |
|---|---|---|
| 0 | 108 | — |
| 5 | 101 | 7 |
| 10 | 98 | 10 |
| 15 | 93 | 15 |
| 20 | 89 | 19 |

TABLE 4

Correlation of drop in $T_m$ with specific activity.

| ENZYME | % EMIM Acetate | % Specific Activity | Melting Temp. (° C.) |
|---|---|---|---|
| T. viride cellulase | 0 | 100 | 65.2 |
| | 2 | 40 | 58.9 |
| | 5 | 60 | 55.4 |
| | 10 | 0 | 49.5 |
| T. maritima endoglucanase | 0 | 100 | 109 |
| | 5 | 77 | 101 |
| | 10 | 65 | 98 |
| | 15 | 50 | 93 |
| | 20 | 45 | 89 |

TABLE 5

Correlation of drop in $T_m$ with specific activity.

| ENZYME | % EMIM Acetate | % Specific Activity | Melting Temp. (° C.) | Melting Temp. Decrease (° C.) |
|---|---|---|---|---|
| T. viride cellulase | 0 | 10 ± 0.8 | — | — |
| | 2 | 6 ± 0.7 | 40 | 6.3 |
| | 5 | 4 ± 0.5 | 60 | 9.8 |
| | 10 | 0 | 0 | 15.7 |
| T. maritima endoglucanase | 0 | 31 ± 2 | — | — |
| | 5 | 24 ± 1 | 23 | 8 |
| | 10 | 20 ± 0.8 | 35 | 11 |
| | 15 | 15 ± 0.5 | 52 | 16 |
| | 20 | 13 ± 0.9 | 58 | 20 |

EXAMPLE 4

Specific Activity in the Presence of [C2mim][OAc]

Figure 6:
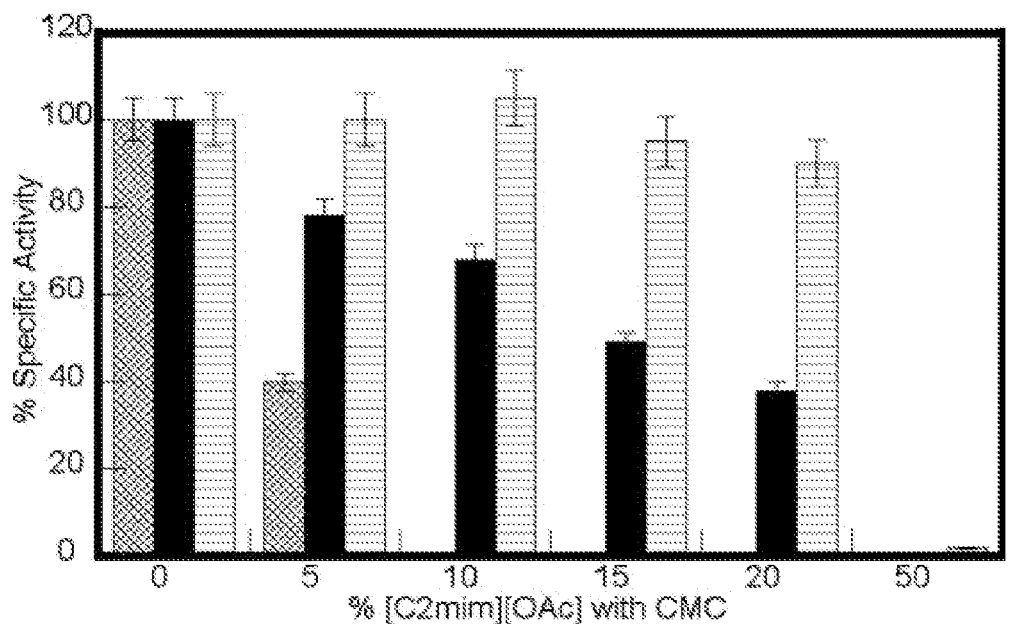
FIG. 6 shows the enzymatic hydrolysis of CMC by cellulase from *T. viride* (cross line), Tma Cel5A (solid) and Pho EG (horizontal line), in the presence of various [C2mim][OAc]: 2% CMC in and 0-50% of [C2mim][OAc] (v/v) were incubated at 37° C. (*T. viride*), 80° C. (TmaEG, Pho EG). The specific activities were calculated as mmoles of reducing sugars formed per min per mg of enzyme. The specific activities are reported as percentages of residual specific activity, taking the specific activity of IL free enzyme a 100% activity. Error bars indicate the standard deviation.

The purified recombinant enzymes are assayed in the presence of [C2mim][OAc] and the specific activity results are compared with the cellulase from T. viride. [C2mim][OAc] was selected as the IL of choice. The assays are performed under optimum pH and temperatures for T. maritima and T. viride enzymes. Optimum pH and temperatures for T. maritima Cel5A is pH 4.8 and 80° C., respectively. Optimum pH and temperatures for T. viride cellulase is pH 4.5 and 37° C., respectively. The Pho EG is assayed at 80° C. where its specific activity is around 10% less than at 95° C. As seen in FIG. 6, the cellulase from T. viride rapidly loses activity with increasing concentration of [C2mim][OAc]. In the presence of 5% (v/v) [C2mim][OAc] the enzyme loses 60% of its activity while it is undetectable in the presence of 10% (v/v) [C2mim][OAc]. Both the recombinant hyperthermophilic enzymes behave very differently. Tma Cel5A in the presence of 5% [C2mim][OAc] loses 24% of its specific activity. At 15% IL (v/v), Tma Cel5A retains 50% of its specific activity. The highest residual activities are observed with Pho EG which retains 100% activity in 20% IL (v/v) (FIG. 6). Preincubation overnight (15 h) in 15% [C2mim][OAc] results in an almost complete loss of activity for the T. viride cellulases while the Tma Cel5A and Pho EG retain 44% and 70% respectively of their activity. The hyperthermophilic enzymes also exhibit longer half-lives, around 20-24 h, compared to the 9 h for the fungal T. viride cellulase, at their optimal pH and temperatures.

EXAMPLE 6

Effect on Pretreated Biomass

Corn stover refers to stalks, leaves and cobs that remain in the fields after the corn kernel harvest and is the largest quantity of biomass residue in the United States and as such is also a LC-biomass source for producing cellulosic ethanol in the United States. [C2mim][OAc] pretreated corn stover is used as a substrate to verify enzymatic efficiency on IL-pretreated biomass and a comparison made with [C2mim][OAc] pretreated Avicel. Avicel is a commercially available microcrystalline cellulose and a good model substrate for analysis. Similar assays are done in the presence of [C2mim][OAc] to simulate real biomass processing and saccharification scenarios. The assay products for the reactions in the presence of IL are detected by high performance anion exchange chromatography (HPAEC). The enzymatic hydrolysis reaction is carried out for 8 h for the T. viride cellulase and 15 h for the hyperthermophilic enzymes, taking into account the half-lives of these enzymes. To compare the amounts of total sugars formed between different reactions, the sum of glucose, xylose and cellobiose are calculated and reported as mmoles of sugars formed per min per mg of enzyme used (Table 7). A comparison of assay results between pretreated and untreated substrate indicates a 2-6 fold increase in hydrolysis products after pretreatment irrespective of the enzyme used, thereby confirming that IL pretreatment can increase the efficiency of hydrolysis of cellulose recovered from biomass. The fungal enzyme is more active on untreated substrates compared to the hyperthermophilic enzymes probably due to the presence of cellobiohydrolases and xylanases in the enzyme mix (Table 7). The catalytic efficiency of the fungal enzyme however, decreases with increasing IL concentration in the reaction mix. After normalizing for the reaction time and enzyme amounts, the amount of sugars formed is undetectable at 15% [C2mim][OAc]. The catalytic efficiencies of the hyperthermophilic enzymes with insoluble substrates and in the presence of [C2mim][OAc] follow a similar trend as seen with the soluble substrate CMC. The yield of sugars from Tma Cel5A hydrolysis of pretreated Avicel in the presence of 15% IL decreases by 43% compared to 0% IL, while the decrease is only 10% in the case of Pho EG on the same substrate under similar conditions (Table 7). Cellobiose is the major product in the case of Pho EG, while a mixture of sugars are obtained for Cel5A.

Table 7 shows the activity assay on insoluble substrates in the absence of [C2mim][OAc] and presence of [C2mim][OAc]. The hydrolysis reactions are performed under pH and temperatures for each enzyme as described herein. The reactions are run over a 14 h period with 5-10 mg of enzyme with 6% (w/v) enzyme loading in optimum buffer for each enzyme and run in duplicate. The reaction products are measured on a HPLC and HPAEC. The amounts of sugars detected are shown in mmoles and normalized with regards to amount of enzyme and time of reaction. Different reactions under each enzyme were run under exactly similar conditions.

Avicel and Corn Stover Pretreatment by [C2mim][OAc].

[C2mim][OAc] (1 kg, as received, <0.2% moisture specified) is heated to 130° C. in a 1.5 L glass reaction vessel with mechanical stirring and 8% w/w (corn stover, 4.8% moisture) or 10% w/w (Avicel PH-101, 3% moisture). After around 3 h when the majority (corn stover) or all (Avicel) has dissolved, the dissolved corn stover or Avicel is allowed to cool to below 80° C. and is added to 2 L of 95% ethanol with rapid agitation to induce the precipitation of dissolved materials. The resulting slurry is filtered under pressure through polypropylene filter cloth and the solids redispersed in 2 L of additional ethanol. The filtration and redispersion steps are repeated twice to remove most residual ionic liquid and the filter cake dried under vacuum at 40° C. to yield a free-flowing powder product. Residual free ionic liquid remaining in the dried biomass is estimated to be less than 4% (w/w).

Enzyme Activity Assays on Soluble and Insoluble Polysaccharides.

Enzymatic activity is measured on soluble polysaccharide substrates, CMC, using the 3,5-dinitrosalicylic acid (DNS) reducing sugar assay. Briefly, 2% CMC (w/v) in 120 mL acetate buffer, (100 mM, pH 4.5 and pH 4.8 for *T. viride* and Tma, respectively, and 100 mM MES buffer, pH 6.4 for *P. hori* EG) is incubated at 80° C. for 30 min for Tma Cel5A and Pho enzymes and 37° C. and 10 min for *T. viride*. The solution is cooled down to 4° C. and 80 mL of DNS solution is added. The reactants are incubated at 95° C. for 5 min and cooled down to room temperature before the absorbance is read at 540 nm. The reducing sugar concentration in the sample is calculated from its absorbance using the standard curve of D-glucose and cellobiose. For hydrolysis reactions in the presence of [C2mim][OAc], control reactions with CMC in the presence of IL but without no enzyme is subtracted from each measurement. The solid substrate (Avicel and corn stover) hydrolysis reactions are conducted at 80° C. for 15 h for the recombinant enzymes and at 37° C. for 8 h in the case of *T. viride* cellulose at the optimum pH for each enzyme. The reaction products are monitored using an Agilent 1200 HPLC equipped with Varian 380-LC Evaporative Light Scattering Detector. The total reaction volumes are 500 mL and shaken at 900 rpm at temperature controlled shakers. Enzyme loadings are 0.4 mg per g of glucan and each data point is measured in triplicate. Separation is achieved using a Varian/Polymer labs Hi-Plex Pb carbohydrate analytical column (300×7.7 mm) with a guard column (50×7.7 mm) at 85° C. (Polymer Laboratories, Varian Inc., Shropshire, UK). The mobile phase is deionized water with a flow rate of 0.6 mL min-1. Hydrolysis reactions in the presence of [C2mim][OAc] are monitored by either by High Performance Anion Exchange Chromatography with Pulsed Amperometric Detection (HPAEC-PAD) on a Dionex DX600 equipped with a Dionex Carbopac PA-20 analytical column (3×150 mm) and a Carbopac PA-20 guard column (3¥30 mm) (Dionex, Sunnyvale, Calif.). Eluent flow rate is 0.4 mL min-1 and the temperature is 30° C. A gradient consisting of a 12 min elution with 14 mM NaOH followed by a 5 min ramp to 450 mM NaOH for 20 min, then a return to the original NaOH concentration of 14 mM for 10 min prior to the next injection. Product concentrations are determined by the integrations of the appropriate peaks from the HPLC or HPAEC chromatograms.

TABLE 7

Activity assay on insoluble substrates in the absence of [C2mim][OAc] and presence of [C2mim][OAc].

| % [C2mim][OAc] | Enzyme | Substrate | Sugars produced $^a$/ $\mu$moles min$^{-1}$ mg$^{-1}$ |
|---|---|---|---|
| 0 | *T. viride* cellulase | Avicel | 3 ± 0.5 |
| | | pAvicel | 5 ± 0.9 |
| | | Corn stover | 2.8 ± 0.8 |
| | | pCorn stover | 6 ± 0.9 |
| | Tma Cel5A | Avicel | 1.1 ± 0.1 |
| | | pAvicel | 6.6 ± 0.8 |
| | | Corn stover | 3 ± 0.9 |
| | | pCorn stover | 9 ± 1 |
| | Pho EG | Avicel | 0.54 ± 0.1 |
| | | pAvicel | 3.2 ± 0.2 |
| | | Corn stover | 0.58 ± 0.1 |
| | | pCorn stover | 2.14 ± 0.1 |
| 5 | *T. viride* cellulase | Avicel | 2.1 ± 0.6 |
| | | pAvicel | 4 ± 0.9 |
| | | Corn stover | 2.3 ± 0.5 |
| | | pCorn stover | 3.6 ± 0.6 |
| | Tma Cel5A | Avicel | 1.0 ± 0.2 |
| | | pAvicel | 6 ± 0.5 |
| | | Corn stover | 2 ± 0.3 |
| | | pCorn stover | 8 ± 0.9 |
| | Pho EG | Avicel | 0.5 ± 0.1 |
| | | pAvicel | 3.3 ± 0.2 |
| | | Corn stover | 0.59 ± 0.1 |
| | | pCorn stover | 2.2 ± 0.14 |
| 10 | *T. viride* cellulase | Avicel | 0.2 ± 0.1 |
| | | pAvicel | 1 ± 0.1 |
| | | Corn stover | 0.6 ± 0.3 |
| | | pCorn stover | 1.1 ± 0.3 |
| | Tma Cel5A | Avicel | 0.9 ± 0.1 |
| | | pAvicel | 5.7 ± 1 |
| | | Corn stover | 2.4 ± 0.8 |
| | | pCorn stover | 7 ± 1 |
| | Pho EG | Avicel | 0.52 ± 0.1 |
| | | pAvicel | 3.1 ± 0.2 |
| | | Corn stover | 0.57 ± 0.1 |
| | | pCorn stover | 2.0 ± 0.2 |
| 15 | *T. viride* celulase | Avicel | <0.01 |
| | | pAvicel | <0.01 |
| | | Corn stover | <0.01 |
| | | pCorn stover | <0.01 |
| | Tma Cel5A | Avicel | 0.6 ± 0.1 |
| | | pAvicel | 4 ± 0.5 |
| | | Corn stover | 2.3 ± 0.5 |
| | | pCorn stover | 5.9 ± 1 |
| | Pho EG | Avicel | 0.6 ± 0.08 |
| | | pAvicel | 2.9 ± 0.06 |
| | | Corn stover | 0.59 ± 0.1 |
| | | pCorn stover | 1.9 ± 0.1 |

$^a$ The sum of glucose, cellobiose and xylose are obtained, normalized by enzyme amount and time.
$^b$ The reactions were spiked with 0 to 15% (v/v) [C2mim][OAc], everything else being the same for all substrates for an enzyme.
$^c$ The sum of glucose, cellobiose and xylose are obtained, normalized by enzyme amount and time.

EXAMPLE 6

Generation and Characterization of Mutant Thermostable Cellulases

Gene Synthesis and Subcloning.

cel5A gene of *Thermatoga maritima* MSB8 (cel5ATm) is synthesized and cloned into pUC57 by GenScript Corporation. Primers, 5'-GAC GAC GAC AAG ATG GGG GTT GAT CCG TTT-3' (SEQ ID NO:18) and 5'-GA GGA GAA GCC CGG TTA TTC GAT ACT GTC ACC GCC-3' (SEQ ID NO:19) (Invitrogen), are used for subcloning cel5ATm into LIC vectors, pET-41 Ek/LIC and pCDF2 Ek/LIC (Novagen) according to the manufacturers' instructions.

Cel5ATm Expression and Purification.

BL21 (DE3) or Acella™ strain (EdgeBio) is used as the host for Cel5ATm expression. The recombinant strain is cultivated in 2×YT autoinduction media (Novagen) containing 50 µg/ml of streptomycin at 37° C. for 20 hours with shaking (250 rpm). The cells are harvested by centrifugation at 8,000 g for 10 min and stored at −80° C. until use.

The cells are added by 1 ml extraction buffer/5 ml cultures (1× BugBuster buffer, Benzonase and Proteinase Inhibitor Cocktail V EDTA free (EMD Chemicals), 1 mg/ml lysozyme (Sigma)) and incubated at 37° C. for 20 min. The extract is centrifuged at 15,000 g for 10 min and the supernatant is heated to 65° C. for 20 min. The denatured proteins are spun down by centrifugation at 15,000 g for 10 min and the supernatant is used for next step purification.

Cel5ATm in the supernatant is purified by Ni-NTA spin columns (Qiagen) according to the manufacturer's instructions. Buffer exchange is carried out by using Vivaspin ultrafiltration units with 10 kDa cutoff (Sartaroius). The enzyme is stored in 50 mM Bis-Tris-HCl buffer (pH 6.5) at −20° C. or −80° C.

Beta-1,4-Endoglucanase (CMCase) Activity Assay.

CMCase activity assay is carried out in 50 mM Bis-Tris-HCl buffer (pH 6.5) containing 1% carboxylmethylcellulose (CMC) and incubated at 75° C. for 30 min. Reducing sugars are analyzed by DNS method as described in Xiao Z, Storms R and Tsang A (2005) "Microplate-based carboxymethylcellulose assay for endoglucanase activity", *Anal. Biochem.* 342: 176-178. Cellobiose is used as reducing sugars standard. 1 U is defined as enzyme amount to produce 1 µmol reducing sugars in one minute at optimal conditions.

Tm Expression Normalization.

pCDF2-cel5ATm clones are picked up from fresh-transformed plates and inoculated into three 96-well deep-well plates (Costar) with 0.9 ml 2×YT with 50 µg/ml of streptomycin, which are incubated at 37° C. with shaking (250 rpm) for 20 hr. These plates are replicated by transferring 36 µl of these over-night cultures into 96-well deep-well plates with 0.9 ml of 2×YT autoinduction medium with 50 µg/ml of streptomycin and incubated at 37° C. with shaking (250 rpm) for 20 hr. The cells are harvested by centrifugation (4,100 rpm) for 10 min and stored at −80° C. 180 µA of extraction buffer are added into each well and incubated the plates at 37° C. with shaking (250 rpm) for 40 min. The cell debris is spun down and the supernatant is transferred into new 96-well plates and stored at 4° C.

5 µl supernatant is mixed with 35 µl sterile ddH₂O and 40 µl 2% CMC in 100 mM Bis-Tris-HCl (pH 6.5) in 96-well PCR plates. These plates are incubated in thermocyclers at 75° C. for 30 min. 80 µl of DNS reagent is added (Ref 1), mixed and incubated at 95° C. for 5 min. The solution is cooled to 4° C. and transferred 100 µl of the products into 96-well plate for reading the ABS at 540 nm.

Random Mutagenesis Library Construction.

Error-prone PCR (ep-PCR) is used for generating mutagenic PCR fragments by using GeneMorph®II Random Mutagenesis Kit (Stratagene). 1 microgram of pET41-LIC-cel5ATm is used as template to carry out low error-rate ep-PCR. Low error-rate library is constructed by LIC cloning resulting PCR fragments into pCDF2 Ek/LIC vector and followed by transformation into Acella™ electroporation cells (EdgeBio) and plating on LB agar plates supplemented with 50 µg/ml of streptomycin.

Mutant Library Analysis.

Clones from the mutant library are analyzed as described for the wild-type of Cel5ATm except that after transferring normal cultures into autoinduction medium, normal culture plates are added by sterile glycerol to 10%, mixed and stored at −80° C. for future investigation. The clones with endoglucanase activity larger than 120% of the wild-type are selected to express the enzymes in 5 ml culture and purified by Ni-NTA columns. Activity improvements are confirmed by detection of their specific activity (U/mg) and plasmids sequencing.

Results.

Thirty-two mutants are picked up from 96-well plates screening and their activity improvements are investigated by the detection of their specific activities. Five mutants, P5C8 (Y66F), P5D8 (N236D), P6H3 (L84M and K123R), P12B12 and P15H11 (S177R), have improved specific activities from 17.58-31.56%.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A composition comprising an ionic liquid that is equal to or less than 20% by volume of the composition and a thermostable cellulase, wherein the thermostable cellulase has at least 90% identity to SEQ ID NO:20 or comprises the amino acid sequence of SEQ ID NO:21.

2. The composition of claim 1, further comprising a cellulose, wherein the thermostable cellulase is capable of hydrolyzing the cellulose.

3. The composition of claim 2, comprising a pretreatment biomass comprising the cellulose.

4. The composition of claim 1, wherein the ionic liquid is equal to or less than 10% by volume of the composition.

5. The composition of claim 4, wherein the ionic liquid is equal to or less than 5% by volume of the composition.

6. The composition of claim 1, wherein the thermostable cellulase is a *Thermatoga maritima* thermostable cellulase mutant with increased cellulase activity, wherein the thermostable cellulase mutant comprises an amino acid sequence having at least 90% identity as compared to the amino acid sequence of SEQ ID NO:20, and comprises at least one amino acid substitution relative to SEQ ID NO:20, at a position selected from D29, K35, D40, I92, E98, E106, A113, E132, N140, K155, S177, E202, E209, L231, A256, K304, and E308.

7. The composition of claim 1, wherein the thermostable cellulose has an optimal temperature that is equal to or more than 65° C.

8. The composition of claim 7, wherein the thermostable cellulose has an optimal temperature that is equal to or more than 85° C.

9. A *Thermatoga maritima* thermostable cellulase mutant with increased cellulase activity, wherein the thermostable cellulase mutant comprises an amino acid sequence having at least 90% identity as compared to the amino acid sequence of SEQ ID NO:20 and comprises at least one amino acid substitution relative to SEQ ID NO:20 at a position selected from D29, K35, D40, I92, E98, E106, A113, E132, N140, K155, S177, E202, E209, L231, A256, K304, and E308.

10. The thermostable cellulase mutant of claim 9, wherein the thermostable cellulase mutant comprises an amino acid sequence depicted by SEQ ID NO:1, 2, 3, 4, 5, 6, 7, 8, or 22.

11. The composition of claim 6, wherein the at least one substitution is selected from E98A, E106D, D40N, L231R, E308K, K155N, A113V, E132D, N140S, E202K, K304N, D29V, I92F, K35N, E209G, A256T, or S177R.

12. The composition of claim 6, wherein the thermostable cellulase mutant comprises an amino acid sequence having at least 95% identity as compared to the amino acid sequence of SEQ ID NO:20.

13. The composition of claim 6, wherein the thermostable cellulase mutant comprises an amino acid sequence selected from SEQ ID NO:1, 2, 3, 4, 5, 6, 7, 8, or 22.

14. The *Thermatoga maritima* thermostable cellulase mutant of claim 9, wherein the mutant comprises an amino acid sequence having at least 95% identity as compared to the amino acid sequence of SEQ ID NO:20.

15. The *Thermatoga maritima* thermostable cellulase mutant of claim 9, wherein the at least one substitution is selected from E98A, E106D, D40N, L231R, E308K, K155N, A113V, E132D, N140S, E202K, K304N, D29V, I92F, K35N, E209G, A256T, and S177R.

* * * * *